United States Patent
Proudfoot et al.

(10) Patent No.: US 7,635,576 B2
(45) Date of Patent: Dec. 22, 2009

(54) CC-CHEMOKINE BINDING TICK PROTEINS

(75) Inventors: Amanda Proudfoot, Chens sur Leman (FR); Christine Power, Thoiry (FR); Achim Frauenschuh, Plan les Ouates/Geneva (CH)

(73) Assignee: Merck Serono SA, Coinsins, Vaud (CH)

( * ) Notice: Subject to any disclaimer, the term of this patent is extended or adjusted under 35 U.S.C. 154(b) by 17 days.

(21) Appl. No.: 11/722,033

(22) PCT Filed: Dec. 19, 2005

(86) PCT No.: PCT/EP2005/056929

§ 371 (c)(1),
(2), (4) Date: Jun. 18, 2007

(87) PCT Pub. No.: WO2006/067124

PCT Pub. Date: Jun. 29, 2006

(65) Prior Publication Data

US 2009/0068173 A1    Mar. 12, 2009

Related U.S. Application Data

(60) Provisional application No. 60/638,312, filed on Dec. 21, 2004.

(30) Foreign Application Priority Data

Dec. 21, 2004 (EP) .................................. 04106778

(51) Int. Cl.
*C12N 15/62* (2006.01)
*C12N 15/63* (2006.01)
*A61K 38/00* (2006.01)
*C07K 14/00* (2006.01)
*C07H 21/04* (2006.01)

(52) U.S. Cl. .................. 435/69.1; 435/71.1; 435/252.3; 435/320.1; 435/69.5; 514/2; 514/12; 530/350; 536/23.4; 536/23.5

(58) Field of Classification Search .................. None
See application file for complete search history.

(56) References Cited

OTHER PUBLICATIONS

Ferreira, B. R. et al. "Antigens from *Rhipicephalus sanguineus* Ticks Elicit Potent Cell-Mediated Immune Responses in Resistant but Not in Susceptible Animals", *Veterinary Parasitology*, 2003, pp. 35-48, vol. 115, No. 1.
Hajnická, V. et al. "Anti-interleukin-8 Activity of Tick Salivary Gland Extracts", *Parasite Immunology*, 2001, pp. 483-489, vol. 23, No. 9.
Database EMBL [Online], EBI Database Accession No. EM_PRO:CK176525, Jul. 2, 2004, XP-002351500, pp. 1-2.
Database EMBL [Online], EBI Database Accession No. EM_PRO:CK179985, Jul. 2, 2004, XP-002351501, pp. 1-2.
Database UniProt [Online], EBI Database Accession No. UniProt:Q7PM27, Mar. 1, 2004, XP-002351499, pp. 1-2.
Database UniProt [Online], EBI Database Accession No. UniProt:Q626N0, Oct. 25, 2004, XP-002351498, pp. 1-2.
Kocakova, P. et al. "Effect of fast protein liquid chromatography fractionated salivary gland extracts from different ixodid tick species on interleukin-8 binding to its cell receptors" *Folia parasitologica*, 2003, pp. 79-84, vol. 50.

*Primary Examiner*—Christine J Saoud
*Assistant Examiner*—Jon M Lockard
(74) *Attorney, Agent, or Firm*—Saliwanchik, Lloyd & Saliwanchik

(57) ABSTRACT

A novel CC-chemokine binding protein is isolated from the saliva of *Rhipicephalus sanguineus*. Compounds prepared in accordance with the present invention can be used as anti-inflammatory compounds and in the treatment or prevention of CC-chemokine-related diseases.

30 Claims, 25 Drawing Sheets

Figure 1

```
  1   GGCCATTACGGCCGGGGGCACATCCACAGGTTCAGTATTAG
      CTGATTGACGTCGTTAGTGGAATTCAACTTGTTTAGCACT

82   ATG ACG TTT AAG GCT TGC ATT GCC ATC ATA
  1   MET THR PHE LYS ALA CYS ILE ALA ILE ILE

112   ACT GCA CTT TGT GCA ATG CAA GTT ATA TGT
 11   THR ALA LEU CYS ALA MET GLN VAL ILE CYS

142   GAA GAT GAT GAA GAT TAT GGA GAC TTA GGA
 21   GLU ASP ASP GLU ASP TYR GLY ASP LEU GLY

172   GGA TGC CCA TTT TTA GTT GCT GAG AAT AAA
 31   GLY CYS PRO PHE LEU VAL ALA GLU ASN LYS

202   ACA GGG TAC CCG ACA ATC GTG GCG TGT AAA
 41   THR GLY TYR PRO THR ILE VAL ALA CYS LYS

232   CAA GAC TGC AAT GGT ACA ACC GAG ACT GCT
 51   GLN ASP CYS ASN GLY THR THR GLU THR ALA

262   CCA AAC GGC ACA CGT TGC TTT TCG ATT GGT
 61   PRO ASN GLY THR ARG CYS PHE SER ILE GLY

392   GAT GAA GGA CTC AGA AGA ATG ACG GCA AAC
 71   ASP GLU GLY LEU ARG ARG MET THR ALA ASN

322   CTT CCT TAC GAC TGC CCT CTA GGA CAA TGC
 81   LEU PRO TYR ASP CYS PRO LEU GLY GLN CYS

352   AGT AAT GGA GAC TGC ATT CCC AAG GAA ACA
```

Figure 1 (continued)

```
 91  SER ASN GLY ASP CYS ILE PRO LYS GLU THR

382  TAC GAG GTA TGC TAC AGA CGC AAT TGG CGA
101  TYR GLU VAL CYS TYR ARG ARG ASN TRP ARG

412  GAC AAG AAG AAT TAA
111  ASP LYS LYS ASN stop  (SEQ ID NO:5)

427  GAATGACCTGATTCCTGGAAAAAAAAAAAAAAAAAAAAAA  (SEQ ID NO:19)
```

Figure 2

```
                    ─────────────────────────▶
                         GCP forward
                         ────────────────────────────────────▶
                                    59-attB1 forward
  1   ggggacaagt ttgtacaaaa aagcaggctt cgccacc atg acgtttaagg cttgcattgc
                                                M   T   F   K   A   C   I 61   catcataact gcactttgtg caatgcaagt tatatgtgaa gatgatgaag attatggaga
      A   I   I   T   A   L   C   A   M   Q   V   I   C   E   D   D   E   D   Y   G 121   cttaggagga tgcccatttt tagttgctga gaataaaaca gggtacccga caatcgtggc
      D   L   G   G   C   P   F   L   V   A   E   N   K   T   G   Y   P   T   I   V 181   gtgtaaacaa gactgcaatg gtacaaccga gactgctcca aacggcacac gttgcttttc
      A   C   K   Q   D   C   N   G   T   T   E   T   A   P   N   G   T   R   C   F 241   gattggtgat gaacgactca gaagaatgac ggcaaacctt ccttacgact gccctctagg
      S   I   G   D   E   G   L   R   R   M   T   A   N   L   P   Y   D   C   P   L 301   acaatgcagt aatggagact gcattcccaa ggaaacatac gaggtatgct acagacgcaa
      G   Q   C   S   N   G   D   C   I   P   K   E   T   Y   E   V   C   Y   R   R
                                                                            ◀────

361   ttggcgagac aagaagaatc accatcacca tcaccat tga acccagctt tcttgtacaa
      N   W   R   D   K   K   N   H   H   H   H   H   H   Stop   (SEQ ID NO:17)
      ◀────────────────────────────
                59-attB2 reverse
                                         ◀────────────────────────────
                                                  GCP reverse
421   agtggtcccc (SEQ ID NO:15)
      ◀────────────
        GCP reverse
```

A

B

C

Figure 6
A)
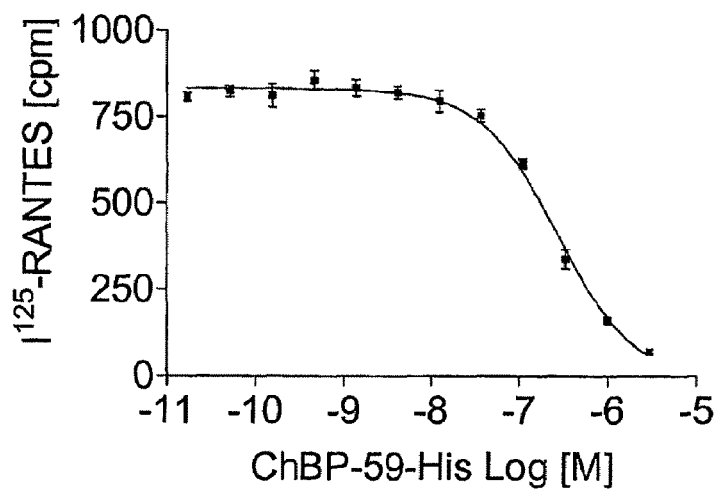
B
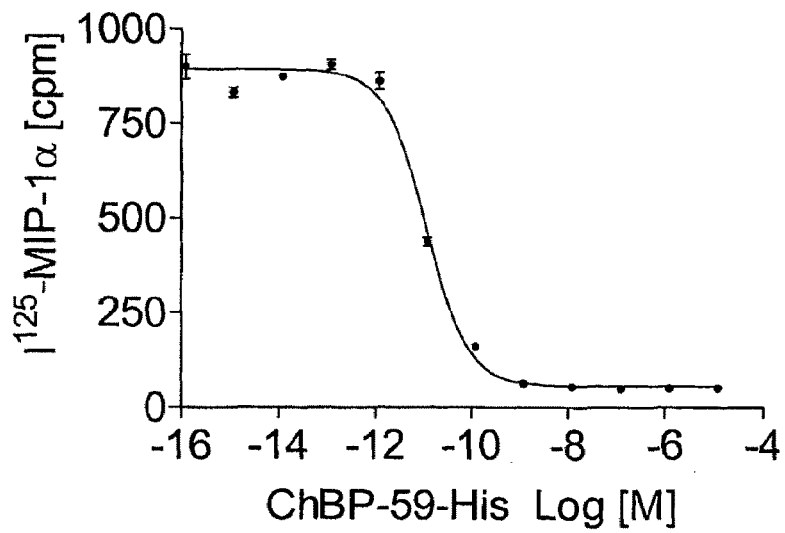

c)

Figure 8
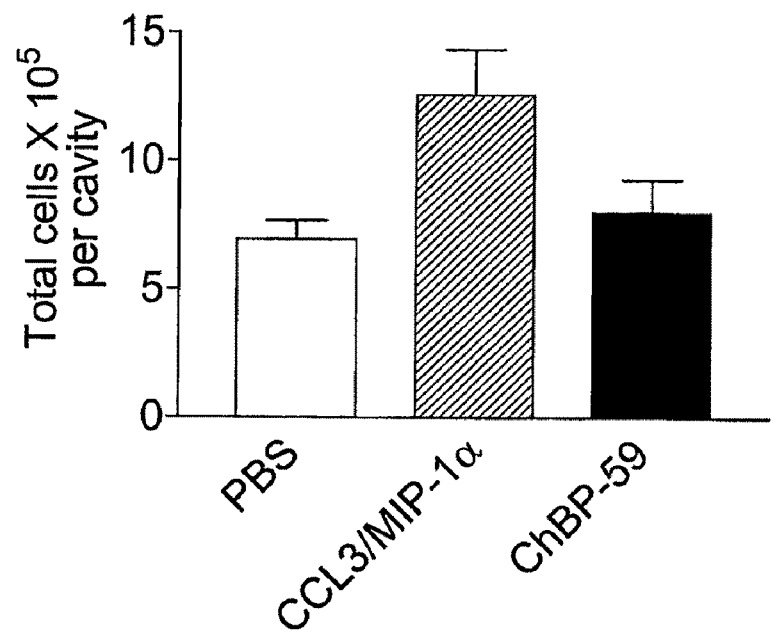
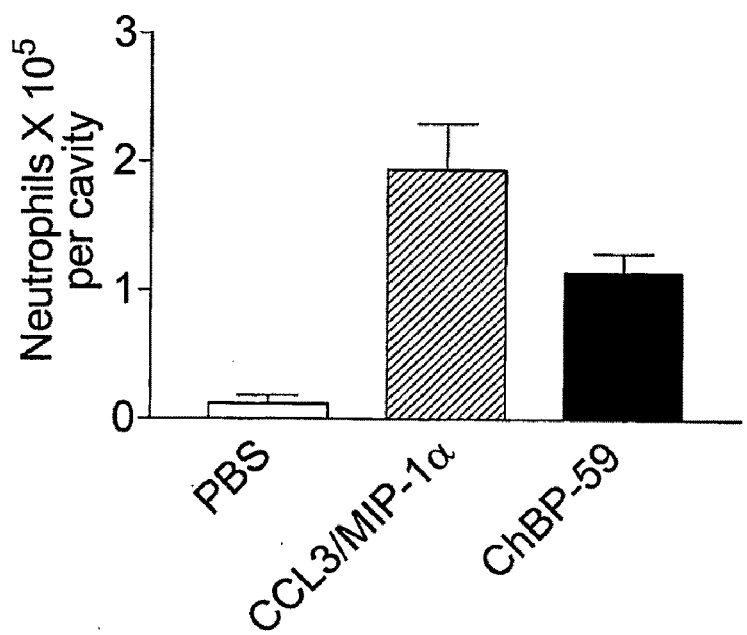

Figure 8 (continued)
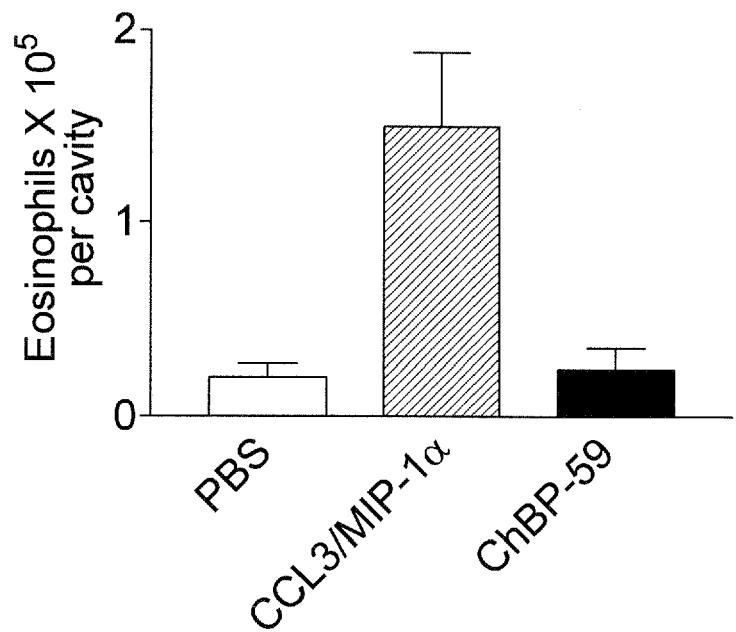
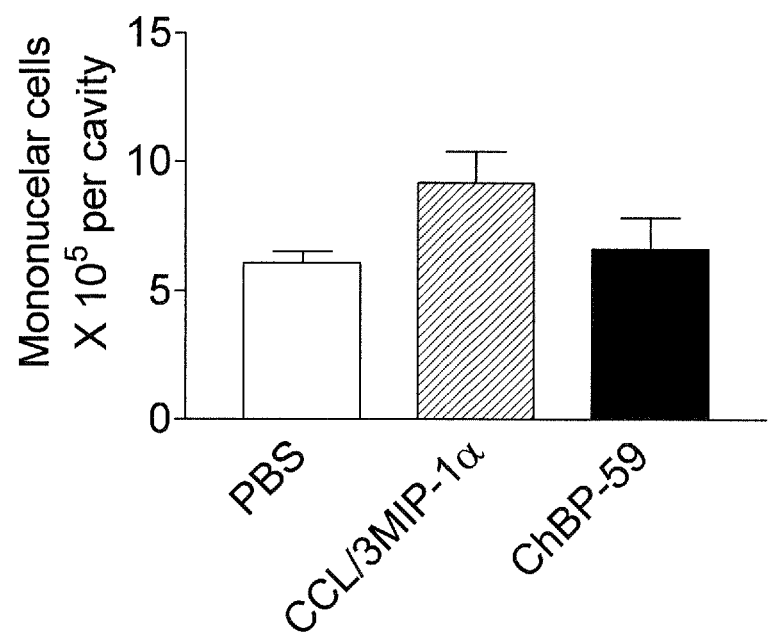

A

Figure 9 (continued)
B
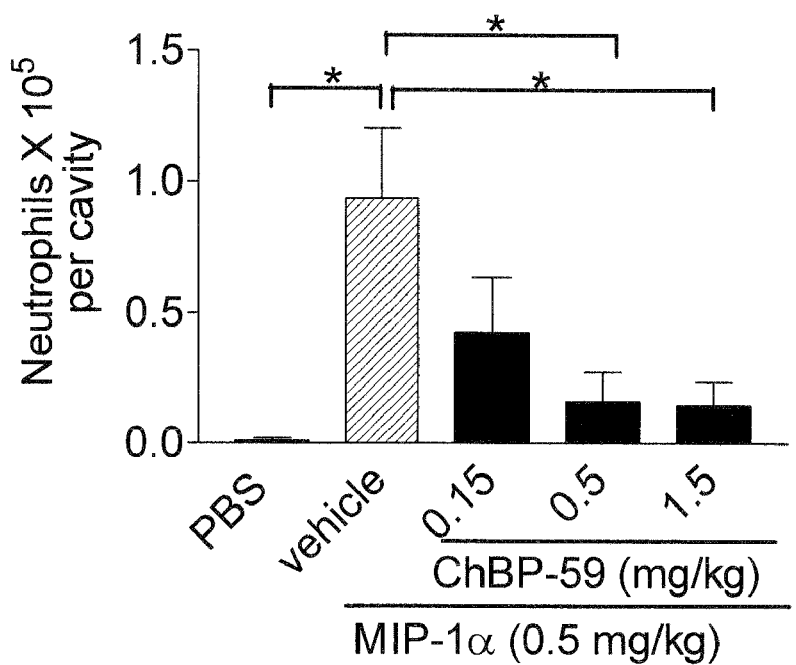
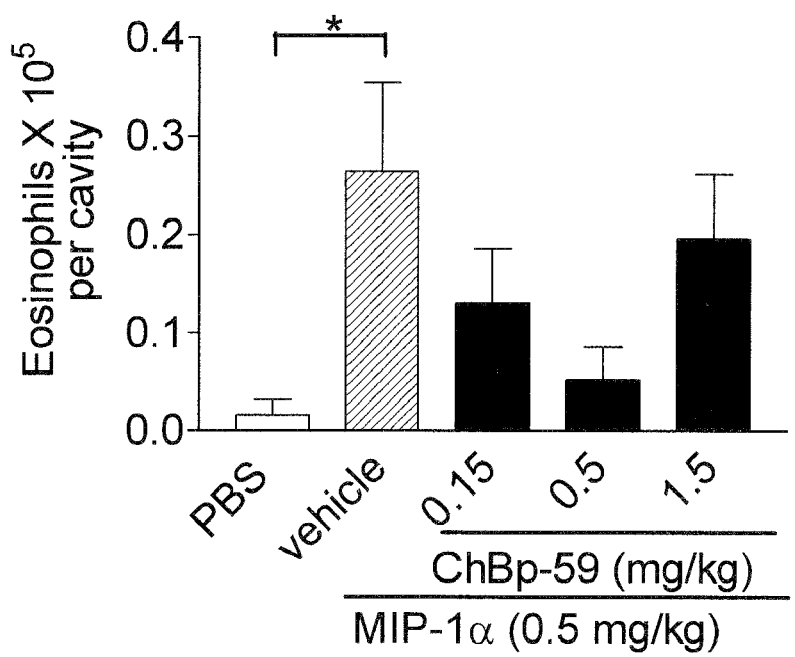

Figure 10
A
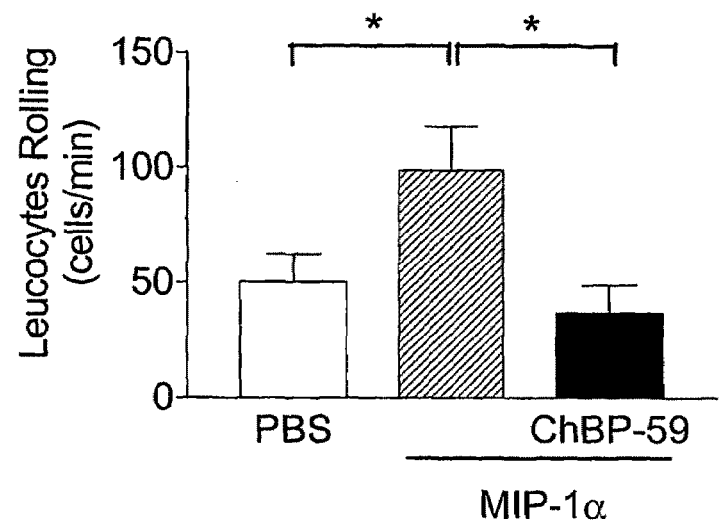
B
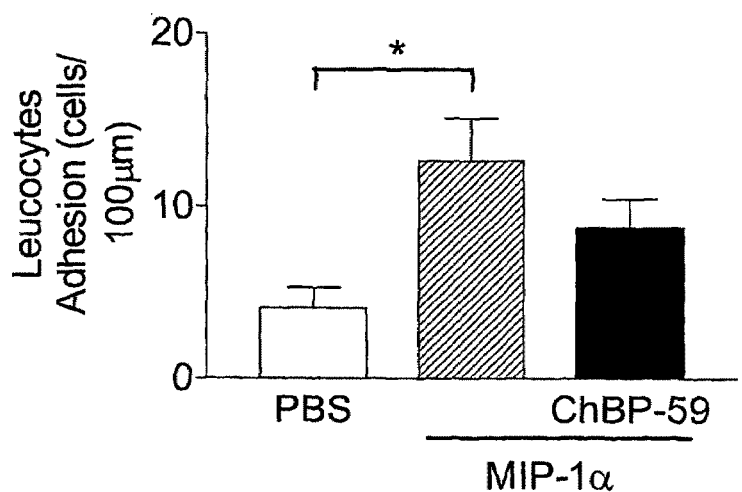

Figure 11
A
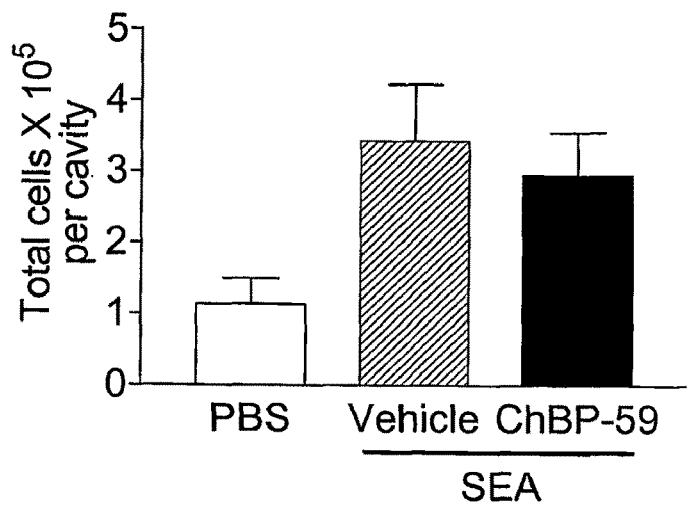
B
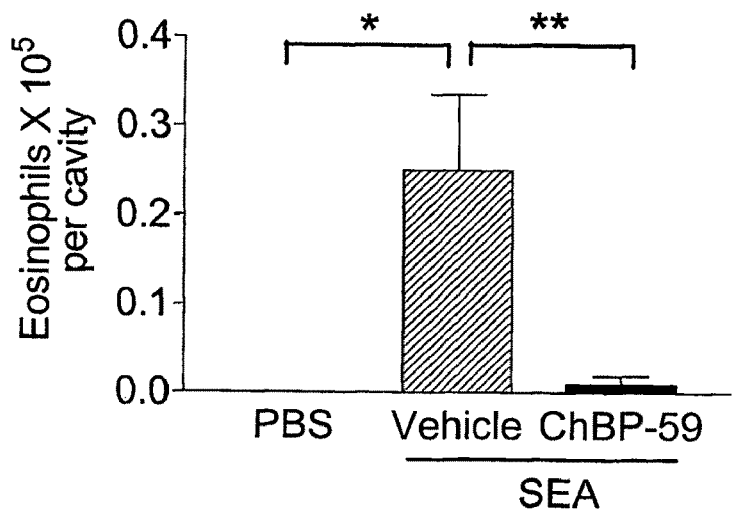

C

Figure 12
A
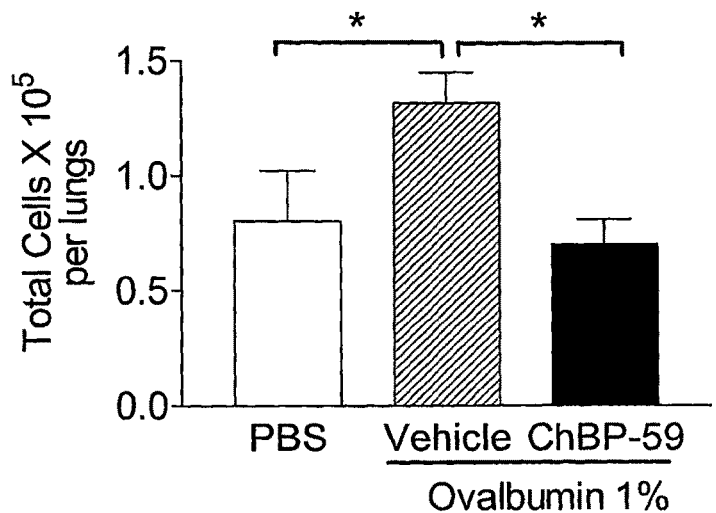
B
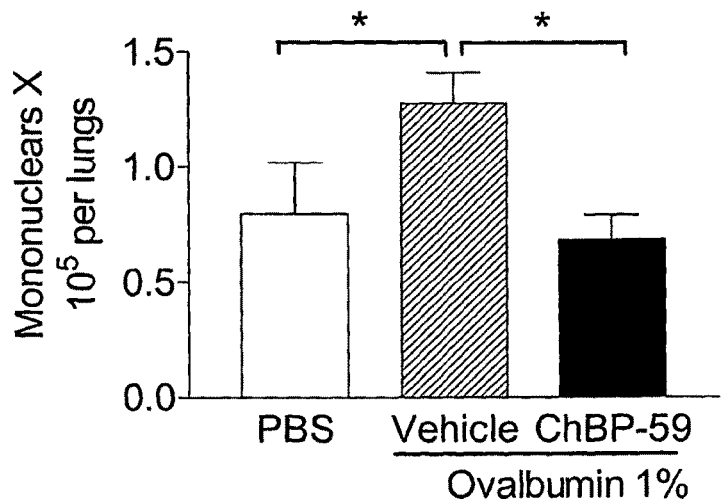

Figure 13
A
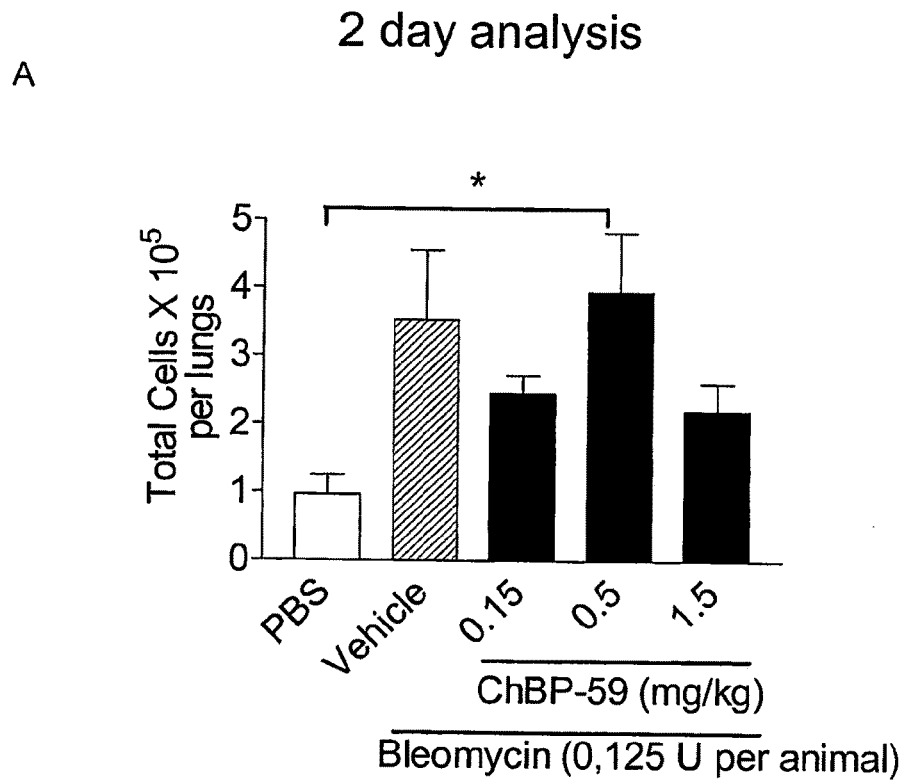
2 day analysis
B
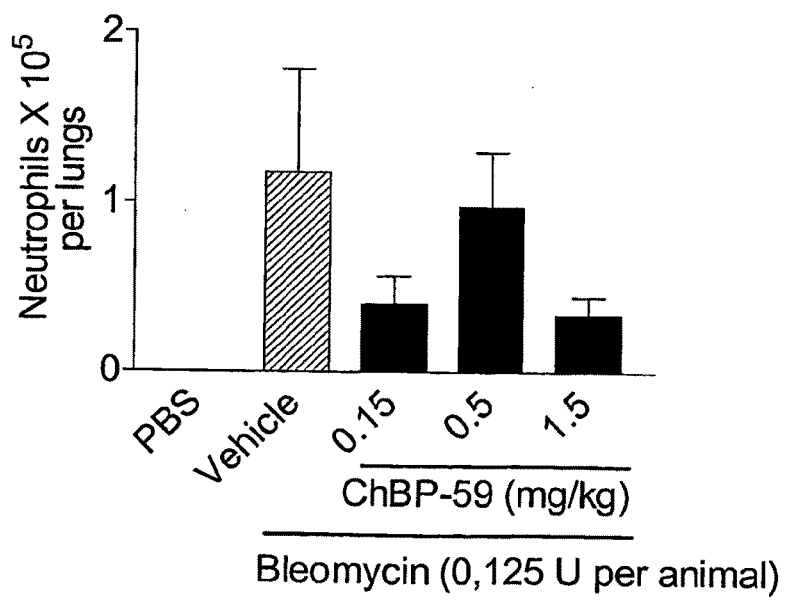

Figure 13 (Continued)
8 day analysis
A
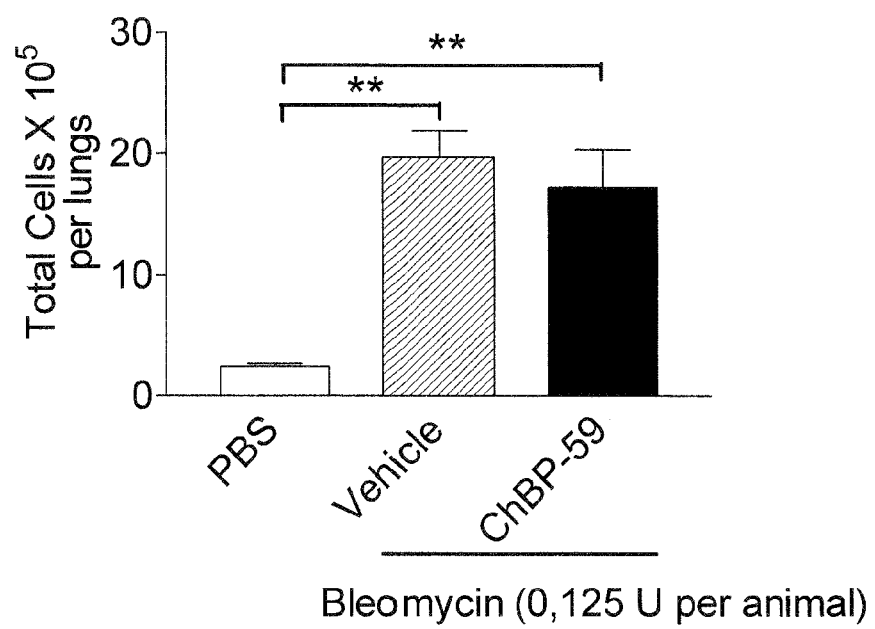
B
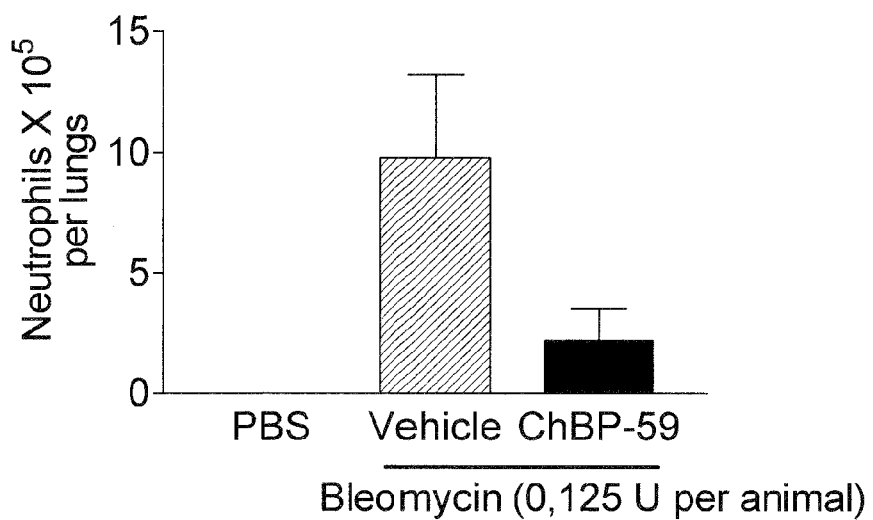

SEQUENCE LISTING

<160> NUMBER OF SEQ ID NOS: 18

<210> SEQ ID NO 1
<211> LENGTH: 247
<212> TYPE: PRT
<213> ORGANISM: Ectromelia virus

<400> SEQUENCE: 1

```
Met Lys Gln Tyr Ile Val Leu Ala Cys Ile Cys Leu Ala Ala Ala Ala
1               5                   10                  15

Ile Pro Thr Ser Leu Gln Gln Ser Phe Ala Ser Ser Cys Thr Glu Glu
            20                  25                  30

Glu Asn Asn His His Met Gly Ile Asp Val Ile Ile Lys Val Thr Lys
        35                  40                  45

Gln Asp Gln Thr Pro Thr Asn Asp Lys Ile Cys Gln Ser Val Thr Glu
    50                  55                  60

Val Thr Glu Ser Glu Asp Asp Gly Val Ser Glu Val Val Lys Gly
65                  70                  75                  80

Asp Pro Thr Thr Tyr Tyr Thr Val Val Gly Gly Gly Leu Arg Met Asn
                85                  90                  95

Phe Gly Phe Thr Lys Cys Pro Gln Ile Lys Ser Ile Ser Glu Ser Ala
            100                 105                 110

Asp Gly Asn Thr Val Asn Ala Arg Leu Ser Ser Val Ser Pro Met Tyr
        115                 120                 125

Gly Ile Glu Ser Pro Ala Ile Thr His Glu Glu Ala Leu Ala Met Ile
    130                 135                 140

Asn Asp Cys Ala Val Ser Ile Asn Ile Lys Cys Ser Glu Glu Glu Lys
145                 150                 155                 160

Asp Ser Asn Ile Lys Thr His Pro Val Leu Gly Ser Asn Ile Ser His
                165                 170                 175
```

-continued

```
Lys Lys Val Arg Tyr Glu Asp Ile Ile Gly Ser Thr Ile Val Asp Ile
            180                 185                 190
Lys Cys Val Lys Asp Leu Glu Phe Ser Val Arg Ile Gly Asp Met Cys
        195                 200                 205
Lys Glu Ala Ser Glu Leu Glu Val Lys Asp Gly Phe Lys Tyr Ile Asp
    210                 215                 220
Gly Ser Val Ser Glu Gly Ala Thr Asp Asp Thr Ser Leu Ile Asp Ser
225                 230                 235                 240
Thr Lys Leu Lys Ala Cys Val
                245
```

<210> SEQ ID NO 2
<211> LENGTH: 744
<212> TYPE: DNA
<213> ORGANISM: Ectromelia virus

<400> SEQUENCE: 2

```
atgaaacaat atatcgtcct ggcatgcata tgcctggcgg cagctgctat ccctaccagt      60
cttcagcaat cattcgcatc ctcgtgtacg gaagaagaaa acaaccatca tatgggaatc     120
gatgttatta tcaaagtcac caagcaagac caaacaccga ctaatgataa gatttgtcaa     180
tcagtaaccg aagttacaga gtctgaagac gatgggggtat ccgaagaagt cgtaaaagga     240
gatcccacca cttattacac tgtcgtcggt ggaggtctga aatgaacttt tggattcacc     300
aaatgtcctc agattaaatc catctcagaa tccgctgatg aaacacagt gaatgctcgg      360
ttgtctagcg tctctccaat gtacggcatt gaatctccag ccatcactca tgaagaagct     420
cttgctatga tcaacgactg tgcggtgtct atcaatatca aatgtagtga agaagagaaa     480
gacagcaaca tcaagaccca tccagtactc gggtctaaca tctctcataa gaaagtgagg     540
tacgaagata tcatcggttc aacgatcgtc gatataaaat gtgtcaagga tctagagttt     600
agcgttcgta tcggagacat gtgcaaggaa gcatctgaac ttgaagtcaa ggatggattc     660
aagtatatcg acggatcggt atctgaaggt gcaaccgatg atacttcact catcgattca     720
acaaaactca aagcgtgtgt ctga                                            744
```

<210> SEQ ID NO 3
<211> LENGTH: 460
<212> TYPE: DNA
<213> ORGANISM: Rhipicephalus sanguineus

<400> SEQUENCE: 3

```
ggccattacg gccgggggca catccacagg ttcagtatta gctgattgac gtcgttagtg      60
gaattcaact tgtttagcac tatgacgttt aaggcttgca ttgccatcat aactgcactt     120
tgtgcaatgc aagttatatg tgaagatgat gaagattatg gagacttagg aggatgccca     180
tttttagttg ctgagaataa acagggtac ccgacaatcg tggcgtgtaa acaagactgc     240
aatggtacaa ccgagactgc tccaaacggc acacgttgct tttcgattgg tgatgaagga     300
ctcagaagaa tgacggcaaa ccttccttac gactgccctc taggacaatg cagtaatgga     360
gactgcattc ccaaggaaac atacgaggta tgctacagac gcaattggcg agacaagaag     420
aattaagaat gacctgattc ctggaaaaaa aaaaaaaaa                            460
```

<210> SEQ ID NO 4
<211> LENGTH: 342
<212> TYPE: DNA
<213> ORGANISM: Rhipicephalus sanguineus

<400> SEQUENCE: 4

```
atgacgttta aggcttgcat tgccatcata actgcacttt gtgcaatgca agttatatgt      60
gaagatgatg aagattatgg agacttagga ggatgcccat ttttagttgc tgagaataaa     120
acagggtacc cgacaatcgt ggcgtgtaaa caagactgca atggtacaac cgagactgct     180
ccaaacggca cacgttgctt ttcgattggt gatgaaggac tcagaagaat gacggcaaac     240
cttccttacg actgccctct aggacaatgc agtaatggag actgcattcc caaggaaaca     300
tacgaggtat gctacagacg caattggcga gacaagaaga at                        342
```

<210> SEQ ID NO 5
<211> LENGTH: 114
<212> TYPE: PRT
<213> ORGANISM: Rhipicephalus sanguineus

<400> SEQUENCE: 5

```
Met Thr Phe Lys Ala Cys Ile Ala Ile Ile Thr Ala Leu Cys Ala Met
1               5                   10                  15
Gln Val Ile Cys Glu Asp Asp Glu Asp Tyr Gly Asp Leu Gly Gly Cys
            20                  25                  30
Pro Phe Leu Val Ala Glu Asn Lys Thr Gly Tyr Pro Thr Ile Val Ala
        35                  40                  45
Cys Lys Gln Asp Cys Asn Gly Thr Thr Glu Thr Ala Pro Asn Gly Thr
    50                  55                  60
Arg Cys Phe Ser Ile Gly Asp Glu Gly Leu Arg Arg Met Thr Ala Asn
65                  70                  75                  80
Leu Pro Tyr Asp Cys Pro Leu Gly Gln Cys Ser Asn Gly Asp Cys Ile
                85                  90                  95
Pro Lys Glu Thr Tyr Glu Val Cys Tyr Arg Arg Asn Trp Arg Asp Lys
            100                 105                 110
Lys Asn
```

<210> SEQ ID NO 6
<211> LENGTH: 94
<212> TYPE: PRT
<213> ORGANISM: Rhipicephalus sanguineus

<400> SEQUENCE: 6

```
Glu Asp Asp Glu Asp Tyr Gly Asp Leu Gly Gly Cys Pro Phe Leu Val
1               5                   10                  15
Ala Glu Asn Lys Thr Gly Tyr Pro Thr Ile Val Ala Cys Lys Gln Asp
            20                  25                  30
Cys Asn Gly Thr Thr Glu Thr Ala Pro Asn Gly Thr Arg Cys Phe Ser
        35                  40                  45
Ile Gly Asp Glu Gly Leu Arg Arg Met Thr Ala Asn Leu Pro Tyr Asp
    50                  55                  60
Cys Pro Leu Gly Gln Cys Ser Asn Gly Asp Cys Ile Pro Lys Glu Thr
65                  70                  75                  80
Tyr Glu Val Cys Tyr Arg Arg Asn Trp Arg Asp Lys Lys Asn
                85                  90
```

<210> SEQ ID NO 7
<211> LENGTH: 39
<212> TYPE: DNA
<213> ORGANISM: Artificial sequence
<220> FEATURE:
<223> OTHER INFORMATION: Primer sequence

```
<400> SEQUENCE: 7
aagcaggctt cgccaccatg acgtttaagg cttgcattg                              39

<210> SEQ ID NO 8
<211> LENGTH: 37
<212> TYPE: DNA
<213> ORGANISM: Artificial sequence
<220> FEATURE:
<223> OTHER INFORMATION: Primer sequence

<400> SEQUENCE: 8
gtgatggtga tggtgattct tcttgtctcg ccaattg                                37

<210> SEQ ID NO 9
<211> LENGTH: 37
<212> TYPE: DNA
<213> ORGANISM: Artificial sequence
<220> FEATURE:
<223> OTHER INFORMATION: Primer sequence

<400> SEQUENCE: 9
ggggacaagt ttgtacaaaa aagcaggctt cgccacc                                37

<210> SEQ ID NO 10
<211> LENGTH: 51
<212> TYPE: DNA
<213> ORGANISM: Artificial sequence
<220> FEATURE:
<223> OTHER INFORMATION: Primer sequence

<400> SEQUENCE: 10
ggggaccact ttgtacaaga aagctgggtt tcaatggtga tggtgatggt g                51

<210> SEQ ID NO 11
<211> LENGTH: 20
<212> TYPE: DNA
<213> ORGANISM: Artificial sequence
<220> FEATURE:
<223> OTHER INFORMATION: Primer sequence

<400> SEQUENCE: 11
gccagcttgg cacttgatgt                                                   20

<210> SEQ ID NO 12
<211> LENGTH: 20
<212> TYPE: DNA
<213> ORGANISM: Artificial sequence
<220> FEATURE:
<223> OTHER INFORMATION: Primer sequence

<400> SEQUENCE: 12
gatggaggtg gacgtgtcag                                                   20

<210> SEQ ID NO 13
<211> LENGTH: 20
<212> TYPE: DNA
<213> ORGANISM: Artificial sequence
<220> FEATURE:
<223> OTHER INFORMATION: Primer sequence

<400> SEQUENCE: 13
tcttctacgg caaggtgctg                                                   20

<210> SEQ ID NO 14
<211> LENGTH: 20
```

<212> TYPE: DNA
<213> ORGANISM: Artificial sequence
<220> FEATURE:
<223> OTHER INFORMATION: Primer sequence

<400> SEQUENCE: 14
aagcaagtaa aacctctaca                                                  20

<210> SEQ ID NO 15
<211> LENGTH: 430
<212> TYPE: DNA
<213> ORGANISM: Artificial sequence
<220> FEATURE:
<223> OTHER INFORMATION: DNA encoding ChBP-59-His fusion protein

<400> SEQUENCE: 15
ggggacaagt ttgtacaaaa aagcaggctt cgccaccatg acgtttaagg cttgcattgc        60
catcataact gcactttgtg caatgcaagt tatatgtgaa gatgatgaag attatgagga       120
cttaggagga tgcccatttt tagttgctga gaataaaaca gggtacccga caatcgtggc       180
gtgtaaacaa gactgcaatg gtacaaccga gactgctcca aacggcacac gttgcttttc       240
gattggtgat gaaggactca agaatgac ggcaaacctt ccttacgact gccctctagg        300
acaatgcagt aatggagact gcattcccaa ggaaacatac gaggtatgct acagacgcaa       360
ttggcgagac aagaagaatc accatcacca tcaccattga aacccagctt tcttgtacaa       420
agtggtcccc                                                             430

<210> SEQ ID NO 16
<211> LENGTH: 360
<212> TYPE: DNA
<213> ORGANISM: Artificial sequence
<220> FEATURE:
<223> OTHER INFORMATION: ORF encoding ChBP-59-His

<400> SEQUENCE: 16
atgacgttta aggcttgcat tgccatcata actgcacttt gtgcaatgca agttatatgt        60
gaagatgatg aagattatgg agacttagga ggatgcccat ttttagttgc tgagaataaa       120
acagggtacc cgacaatcgt ggcgtgtaaa caagactgca atggtacaac cgagactgct       180
ccaaacggca cacgttgctt ttcgattggt gatgaaggac tcagaagaat gacggcaaac       240
cttccttacg actgccctct aggacaatgc agtaatggag actgcattcc caaggaaaca       300
tacgaggtat gctacagacg caattggcga gacaagaaga atcaccatca ccatcaccat       360

<210> SEQ ID NO 17
<211> LENGTH: 120
<212> TYPE: PRT
<213> ORGANISM: Artificial sequence
<220> FEATURE:
<223> OTHER INFORMATION: ChBP-59-HIS fusion protein

<400> SEQUENCE: 17

Met Thr Phe Lys Ala Cys Ile Ala Ile Ile Thr Ala Leu Cys Ala Met
1               5                   10                  15

Gln Val Ile Cys Glu Asp Asp Glu Asp Tyr Gly Asp Leu Gly Gly Cys
            20                  25                  30

Pro Phe Leu Val Ala Glu Asn Lys Thr Gly Tyr Pro Thr Ile Val Ala
        35                  40                  45

Cys Lys Gln Asp Cys Asn Gly Thr Thr Glu Thr Ala Pro Asn Gly Thr
    50                  55                  60

```
                                       -continued

Arg Cys Phe Ser Ile Gly Asp Glu Gly Leu Arg Arg Met Thr Ala Asn
 65              70                  75                  80

Leu Pro Tyr Asp Cys Pro Leu Gly Gln Cys Ser Asn Gly Asp Cys Ile
                 85                  90                  95

Pro Lys Glu Thr Tyr Glu Val Cys Tyr Arg Arg Asn Trp Arg Asp Lys
            100                 105                 110

Lys Asn His His His His His His
            115                 120

<210> SEQ ID NO 18
<211> LENGTH: 100
<212> TYPE: PRT
<213> ORGANISM: Artificial sequence
<220> FEATURE:
<223> OTHER INFORMATION: Mature form of ChBP-59-HIS fusion protein

<400> SEQUENCE: 18

Glu Asp Asp Glu Asp Tyr Gly Asp Leu Gly Gly Cys Pro Phe Leu Val
 1               5                  10                  15

Ala Glu Asn Lys Thr Gly Tyr Pro Thr Ile Val Ala Cys Lys Gln Asp
            20                  25                  30

Cys Asn Gly Thr Thr Glu Thr Ala Pro Asn Gly Thr Arg Cys Phe Ser
             35                 40                  45

Ile Gly Asp Glu Gly Leu Arg Arg Met Thr Ala Asn Leu Pro Tyr Asp
        50                  55                  60

Cys Pro Leu Gly Gln Cys Ser Asn Gly Asp Cys Ile Pro Lys Glu Thr
 65              70                  75                  80

Tyr Glu Val Cys Tyr Arg Arg Asn Trp Arg Asp Lys Lys Asn His His
                 85                  90                  95

His His His His
            100
```

CC-CHEMOKINE BINDING TICK PROTEINS

CROSS-REFERENCE TO RELATED ANPLICATION

This application is the U.S. national stage application of International Patent Application No. PCT/EP2005/056929, filed Dec. 19, 2005, which claims the benefit of U.S. Provisional Patent Application No. 60/638,312, filed Dec. 21, 2004, the disclosures of which are hereby incorporated by reference in their entireties, including all figures, tables and amino acid or nucleic acid sequences.

FIELD OF THE INVENTION

The invention relates to novel antagonists of CC-chemokines and their uses, particularly as anti-inflammatory compounds and in the treatment or prevention of CC-chemokine-related diseases.

BACKGROUND OF THE INVENTION

Chemokines are small, secreted pro-inflammatory proteins, which mediate directional migration of leukocytes from the blood to the site of injury. Depending on the position of the conserved cysteines characterizing this family of proteins, the chemokine family can be divided structurally into C, CC, CXC and $CX_3C$ chemokines that bind to a series of membrane receptors (Baggiolini M et al., 1997; Fernandez EJ and Lolis E, 2002). These membrane receptors, all heptahelical G-protein coupled receptors, allow chemokines to exert their biological activity on the target cells, which may present specific combinations of receptors according to their state and/or type. The physiological effects of chemokines result from a complex and integrated system of concurrent interactions: the receptors often have overlapping ligand specificity, so that a single receptor can bind different chemokines. A single chemokine can bind to different receptors as well.

Studies on structure-activity relationships indicate that chemokines have two main sites of interaction with their receptors, the flexible amino-terminal region and the conformationally rigid loop that follows the second Cysteine. Chemokines are thought to dock onto receptors by means of the loop region, and this contact is believed to facilitate the binding of the amino-terminal region that results in receptor activation.

Usually, chemokines are produced at the site of injury and cause leukocyte migration and activation, playing a fundamental role in inflammatory, immune, homeostatic, hematopoietic, and angiogenic processes. Thus, these molecules are considered good target candidates for therapeutic intervention in diseases associated with such processes. The inhibition of chemokines, or of their receptors, can reduce leukocyte maturation, recruitment and activation, as well as other pathological processes related to angiogenesis or arteriosclerosis (Baggiolini M, 2001; Loetscher P and Clark-Lewis I, 2001; Godessart N and Kunkel SL, 2001).

In addition to mutant inhibitory chemokines, antibodies and peptide and small molecule inhibitors blocking the receptors the search for effective chemokine antagonists has also been extended to a series of viruses and other organisms that, when entering into contact with human or mammal hosts, show potent immunomodulatory activities affecting the host. The viral mimicry of cytokines, chemokines, and their receptors may indicate strategies of immune modulation for developing therapeutic products (Alcami A, 2003; Lindow M et al., 2003). Recently, immunomodulatory factors expressed by haematophagous arthropods (such as mosquitoes, sandflies and ticks) have been reviewed (Gillespie, RD et al., 2000).

In particular, the salivary glands of ticks produce a complex mixture of bioactive molecules having, in particular, anti-inflammatory, anti-haemostatic and anti-immune activities. These include bioactive proteins that control histamine, bind immunoglobulins, or inhibit the alternative complement cascade or other proteases.

Despite the large amount of literature, only a few articles list cDNA sequences identified by random sequencing and differential screens of libraries generated from various tick tissues and/or species. However, the large majority of these sequences are not characterized biochemically or functionally, and many annotations are entered only on the basis of sequence similarity with known proteins involved in basic cellular functions, such as those previously characterised in tick salivary glands for enzymatic activities or inducing antibody response. In particular, there is no indication of tick proteins acting as CC-chemokine binding proteins and functioning as CC-chemokine antagonists.

SUMMARY OF THE INVENTION

Surprisingly, it has been found that the saliva of *Rhipicephalus sanguineus* (dog tick) contains a novel protein termed ChBP-59, which binds CC-chemokines and inhibits their activity. ChBB-59 was cloned from a *Rhipicephalus sanguineus* cDNA library, and expressed in mammalian cells. This protein, as well as derivatives, fragments or mimetics thereof, can be used therapeutically, e.g., as antagonists of CC-chemokines in mammalian organisms, or as targets for vaccination and for the control of ticks and of tick-borne pathogens.

A first aspect of the invention thus relates to a polypeptide comprising the amino acid sequence of ChBP-59 or of a fragment or analog thereof. Preferred polypeptides of this invention bind a CC-chemokine, and inhibit its biological activity. A specific example of such a polypeptide is ChBP-59 or a fragment thereof.

A second aspect of the invention relates to nucleic acid molecules encoding a polypeptide as defined above. Such nucleic acids also include oligonucleotides isolated from them and vectors containing said molecules, in particular expression vectors.

A third aspect of this invention resides in antibodies that selectively bind the polypeptides as defined above.

A fourth aspect of this invention relates to host cells and transgenic non-human animals expressing a polypeptide as defined above, as well as methods of producing such cells and transgenic non-human animals.

A fifth aspect of this invention is a process for preparing a polypeptide as defined above, typically using recombinant technologies.

A sixth aspect of the invention is a pharmaceutical (including a vaccine or immunogenic) composition comprising a polypeptide or nucleic acid molecule as defined above and a pharmaceutically acceptable carrier or vehicle.

A seventh aspect of the invention relates to the use of a polypeptide or nucleic acid molecule as defined above as a medicament, in particular for the preparation of a medicament for regulating an immune or inflammatory response in a mammal, as well as to corresponding methods for treatment.

Other features and advantages of the invention will be apparent from the following detailed description.

DESCRIPTION OF THE FIGURES

FIG. 1: Alignment of ChBP-59 cDNA sequence with ChBP-59 protein sequence encoded by the relevant Open Reading Frame (ORF). The signal sequence (residues 1-20, as predicted by the algorithm SIGNALJ) is underlined. The predicted polyadenylation site is boxed. The Cysteine residues present in the mature protein are highlighted. The predicted N-linked glycosylation sites are in bold.

FIG. 2: Alignment of the Gateway compatible ChBP-59 cDNA containing the flanking attB sites obtained by two successive rounds of PCR. The arrows indicate the position and sense of the relevant PCR primers (summarized in Table III). Start and stop codons are in bold. The amino acids forming the signal sequence are underlined.

FIG. 8: Inhibitory effect of ChBP-59-6His on CCL3/MIP-1α induced peritoneal recruitment. ChBP-59-6His was administered s.c. at a dose of 1.5 mg/kg 45 min before the administration of CCL3/MIP-1α at 0.15 mg/kg i.p. After 18 h the mice were sacrificed and the number of cells recruited into the peritoneal cavity were enumerated.

DETAILED DESCRIPTION OF THE INVENTION

Figure 3:
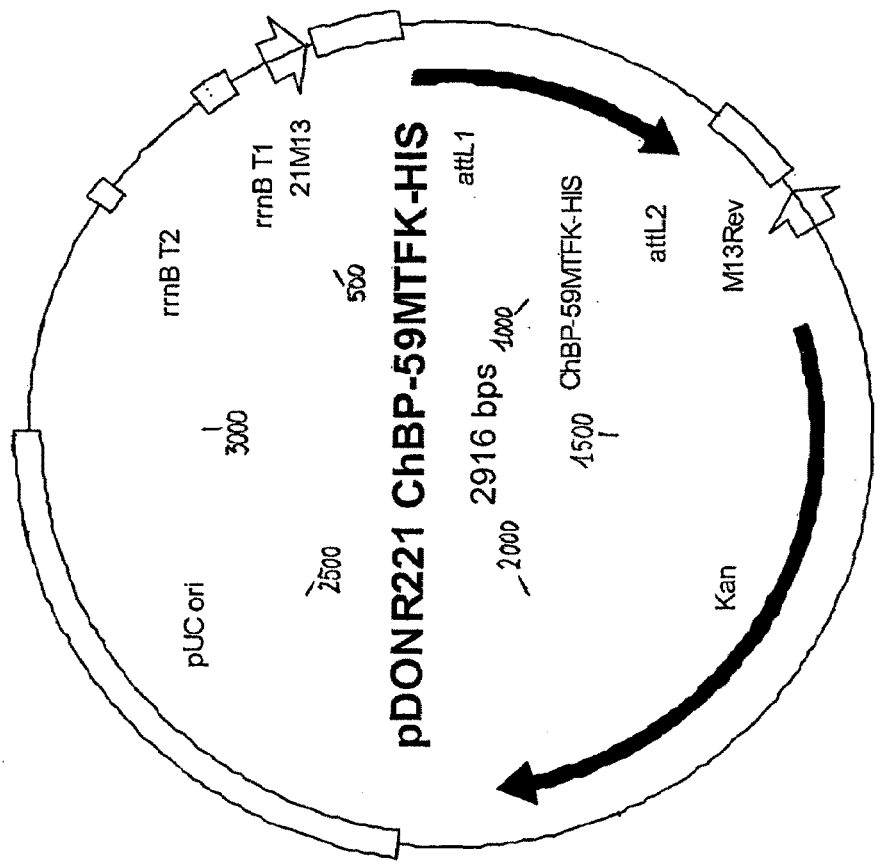
FIG. 3: (A) Map of the pDONR221_ChBP-59-HIS entry vector for Gateway cloning system. (B) Map of the pDEST8_ChBP-59-HIS expression vector for expression in insect (TN5) cells. (C) Map of the pEAK12d_ChBP-59-HIS expression vector for expression in mammalian (HEK293/EBNA) cells.
Figure 3:
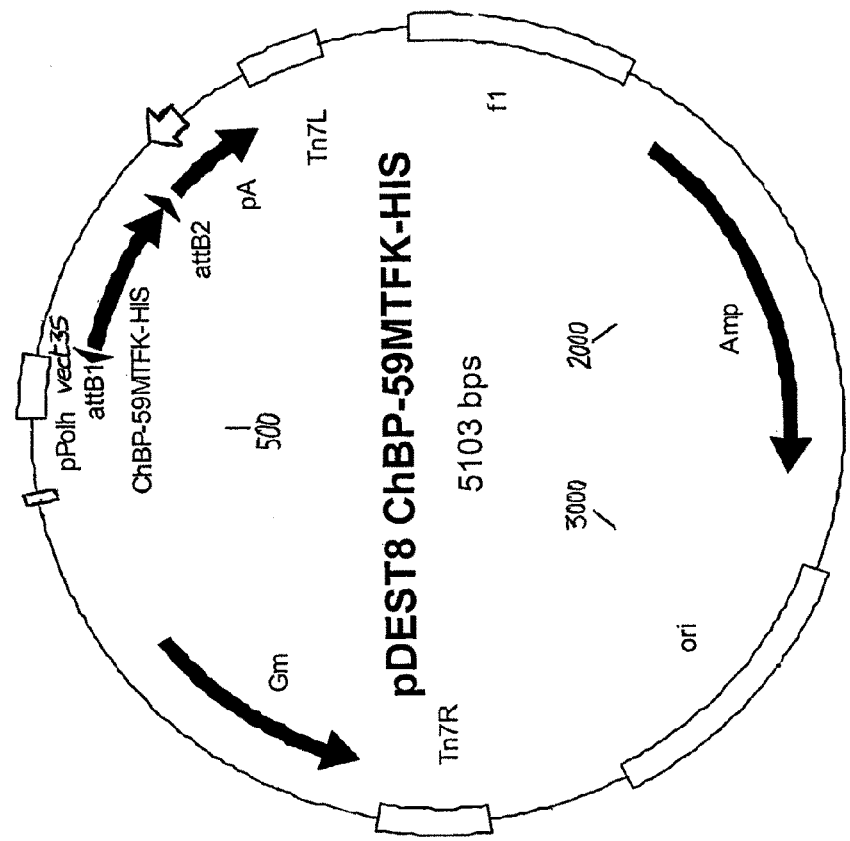
Figure 3:
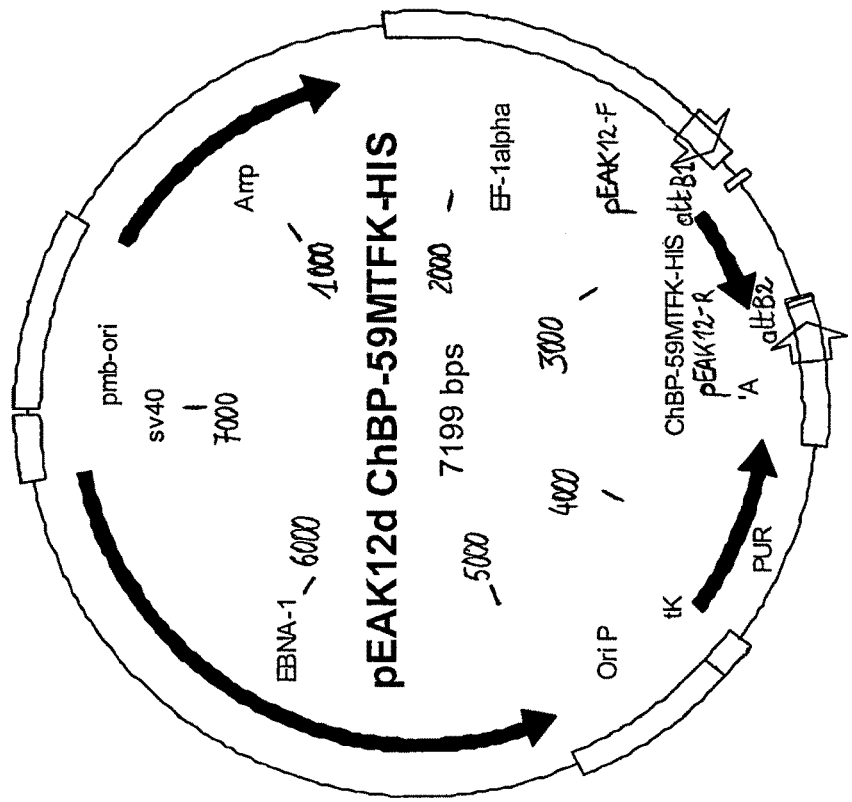

The present invention provides novel compositions and methods for regulating chemokine activity. More particularly, the present invention discloses novel protein having CC-chemokine binding properties, that can be used to inhibit chemokine action. The examples show that this protein, derived from tick saliva, can be expressed and purified in recombinant form, and effectively binds CC-chemokines and inhibits their action, e.g., the specific chemotactic response of cells induced by a CC-chemokine.

A first aspect of the invention thus resides in a ChBP-59 polypeptide, i.e., any polypeptide comprising the amino acid sequence of ChBP-59 or of a fragment or analog thereof. Preferred polypeptides of this invention bind a CC-chemokine, and inhibits the activity of said the chemokine. Particular polypeptides of this invention are selected from the group consisting of:

a) a protein comprising an amino acid sequence of ChBP-59 (SEQ ID NO: 5);

b) a protein comprising an amino acid sequence of mature ChBP-59 (SEQ ID NO: 6);

c) a protein comprising an amino acid sequence of ChBP-59-HIS (SEQ ID NO: 17);

d) a protein comprising an amino acid sequence of mature ChBP-59-HIS (SEQ ID NO: 18);

e) a protein encoded by a nucleic acid molecule capable of hybridization to a nucleic acid sequence encoding a protein of a), b), c) or d) under moderately stringent conditions, said nucleic acid molecule encoding a protein that binds a CC-chemokine and inhibits the activity of said chemokine;

f) a protein at least about 70% identical in amino acid sequence to a protein of a), b), c), or d), and that binds a CC-chemokine and inhibits the activity of said chemokine;

g) a protein comprising a fragment of a protein of a), b), c), d), e), or f), which fragment retains the ability to bind a CC-chemokine and inhibit the activity of said chemokine; and h) a protein comprising a fragment of a protein of a), b), c), d), e), or f), which fragment has an immunomodulatory activity.

In a preferred embodiment, the protein is selected from the group consisting of:

a) a protein having an amino acid sequence of ChBP-59 (SEQ ID NO: 5);

b) a protein having an amino acid sequence of mature ChBP-59 (SEQ ID NO 6);

c) a protein having an amino acid sequence of ChBP-59-HIS (SEQ ID NO: 17);

d) a protein having an amino acid sequence of mature ChBP-59-HIS (SEQ ID NO: 18);

e) a protein comprising a fragment of a protein of a), b), c), or d), which fragment binds a CC-chemokine and inhibits the activity of said chemokine;

f) a protein comprising a fragment of a protein of a), b), c), or d), which fragment has an immunizing activity when administered to a mammal.

In another aspect, the invention relates to an active mutant of a protein defined above, in which mutant one or more amino acid residues have been added, deleted, or substituted and which mutant binds a CXC-chemokine and inhibits the activity of said chemokine.

The polypeptides of the invention can be in a mature form, resulting from one or more post-translational modifications (glycosylation, phosphorylation, modification with endo-/exopeptidases for eliminating the signal peptide, for example) or from the in-frame addition of sequence encoding heterologous sequences (such as tags or domains that improve the detection and/or the purification). For example, ChBP-59 has been expressed as a recombinant histidine-tagged protein in the complete (SEQ ID NO: 17) and mature form (SEQ ID NO: 18), in both a mammalian and an insect cell line.

The polypeptides of this invention or their corresponding nucleic acids may be in isolated form (e.g., not in their natural environment), including recombinant or synthetic polypeptides and nucleic acids.

The examples show that ChBP-59 polypeptides bind CC-chemokines and can be used to inhibit (e.g., reduce) their activity. This characterization was performed by making use of a series of biochemical assays, including the use of radioactive CC-chemokines, or functional assays including cell based assays as well as in vivo animal disease models. As demonstrated in the examples, ChBP-59 polypeptides bind in particular CC-chemokines such as CCL5/RANTES, CCL3/MIP-1 alpha, or CCL2/MCP-1, or in general to CC-chemokines that bind CCR1 or CCR5 receptors. The ChBP-59 protein can be considered as a broad spectrum CC-chemokine binding protein, recognizing other CC-chemokines such as TARC/CCL17, CCL18/PARC, CCL4/MIP-1 beta, MDC/CCL22, MCP-3/CCL7, MCP-2/CCL7, and Eotaxin/CCL11, albeit with different activities. Such spectrum of activity confer to the ChBP-59 polypeptides of this invention a broad range of therapeutic utility, as discussed below.

Within the context of the present invention, a fragment of a polypeptide designates any fragment comprising at least 5, 7, 7, 8, 9 or 10 consecutive amino acid residues of said polypeptide sequence. Particular fragments of this invention comprise 15, 20, 25 or more amino acid residues of a ChBP-59 protein as disclosed therein. Preferred fragments retain the ability to bind a chemokine at least one biological activity of a full-length protein, e.g., a an immunogenic activity or an immunomodulatory activity.

In this regard, within the context of the present invention, an "immunomodulatory activity" designates any activity detected in vitro or in vivo that affects the immune response in either a positive or negative manner. Examples of such activities are immunizing activities, immunosuppressive activities, anti-inflammatory activities, pro-/anti-apoptotic activities, or anti-tumoral activities.

Alternatively the fragment can be identified as providing an immunizing activity when administered to a mammal. These fragments should have appropriate antigenic, immunogenic properties for raising an immune response when needed (for example, against ticks or tick-borne pathogenic organisms). The literature provides many examples on how such functional sequences can be identified as candidate vaccine antigens, and eventually administered with adjuvants and/or cross-linked to a carrier. (Mulenga A et al. 2000; WO 01/80881; WO 03/030931; WO 01/87270). A specific antigen or group of antigens identified in ChBP-59 can be used for preventing or reducing ectoparasite infection or disease in an animal, so that the immunity of the animal to the ectoparasite is boosted by natural challenge of the animal with the ectoparasite (WO 95/22603). Finally, the fragment can be also used for raising antibodies directed to the entire protein for screening or diagnostic applications.

The properties of ChBP-59 defined above, and exemplified herein using recombinant variants of this sequence, can be maintained, or even potentiated, in the active mutants. This category of molecules includes natural or synthetic analogs of said sequence, wherein one or more amino acid residues have been added, deleted, or substituted, provided they display the same biological activity characterized in the present invention at comparable or higher levels, as determined by means disclosed in the Examples below.

In particular, the term "active" means that such alternative compounds should maintain, or even potentiate, the CC-chemokine binding and immunomodulatory properties of ChBP-59.

Active mutant molecules can be generated by site-directed mutagenesis techniques, combinatorial technologies at the level of encoding DNA sequence (such as DNA shuffling, phage display/selection), or by computer-aided design studies, or any other known technique suitable thereof, which provide a finite set of substantially corresponding mutated or shortened peptides or polypeptides. These alternative molecules can be routinely obtained and tested by one of ordinary skill in the art using the teachings presented in the prior art and in the Examples below.

In accordance with the present invention, preferred changes in these active mutants are commonly known as "conservative" or "safe" substitutions, and involve non-basic residues. Conservative amino acid substitutions are those with amino acids having sufficiently similar chemical properties, in order to preserve the structure and the biological function of the molecule. It is clear that insertions and deletions of amino acids may also be made in the above defined sequences without altering their function, particularly if the insertions or deletions only involve a few amino acids, e.g., under ten, and preferably under three, and do not remove or displace amino acids which are critical to the functional conformation of a protein or a peptide.

The literature provides many models on which the selection of conservative amino acids substitutions can be performed on the basis of statistical and physico-chemical studies on the sequence and/or the structure of natural protein (Rogov SI and Nekrasov AN, 2001). Protein design experiments have shown that the use of specific subsets of amino acids can produce foldable and active proteins, helping in the classification of amino acid "synonymous" substitutions which can be more easily accommodated in the protein structure, and which can be used to detect functional and structural ChBP-59 homologs and paralogs (Murphy LR et al., 2000). The synonymous amino acid groups and more preferred synonymous groups for the substitutions are those defined in Table I.

However, in the context of ChBP-59 sequence, specific residues may have a particular importance. For example, ChBP-59 is not significantly homologous to any known proteins but contains a pair number of cysteine residues in the mature protein, in particular in the position corresponding to 32, 49, 53, 66, 85, 90, 95, and 104 in full length ChBP-59 according to SEQ ID NO: 5. Moreover, ChBP-59 contains three potential glycosylation sites in the position corresponding to Asparagine 39, 54, and 62 of full length ChBP-59 according to SEQ ID NO: 5. These residues may be important for the correct folding and/or activity and should be preferably conserved in the corresponding positions of these alternative polypeptides. Alternatively, the deleted or substituted cysteines or glycosilation sites can be re-established in a different position of the protein.

Alternatively, active mutants of ChBP-59 may result from sequence alterations reducing the immunogenicity of said CC-chemokine binding protein when administered to a mammal. The literature provides many examples of these sequence alterations that can be designed and introduced at this scope or for other functional optimizations that allow a safe and effective administration of a therapeutic protein, especially when it is a non-human, non-mammalian, or non-natural protein (Schellekens H, 2002). Example of technical approaches for achieving these molecules are directed evolution (Vasserot AP et al., 2003), rational design (Marshall SA et al., 2003), bioinformatics (Gendel SM, 2002), the identification and the neutralization of CD4+ T-cell epitopes (WO 03/104263; WO 03/006047; WO 02/98454; WO 98/52976; WO 01/40281), fusion with other protein sequences (WO 02/79415; WO 94/11028), or conjugation with other compounds (WO 96/40792).

Active ChBP-59-derived sequences can be natural analogs or orthologs of ChBP-59 that may be isolated from, in particular, other tick species, in particular those belonging to the Ixodidae family, and more in particular to the subfamiliy Rhipicephalinae, to which *Rhipicephalus sanguineus* belongs, as well to other subfamilies like Ixodinae (including *Ixodes scapularis* and *Ixodes ricinus*) or Amblyomminae (including *Amblyomma variegatum* and *Amblyomma americanum*). Alternatively, orthologs may be identified in mammalians, such as man and mouse.

Limited information is available on the genome and the transcriptome of haematophagous arthropods, and is mostly associated with ribosomal and mitochondrial sequences, which were studied to determine the phylogenetic relationships on the basis of their conservation (Murrell A et al., 2001). Tick genomic data are available only in partial and preliminary formats (Ullmann AJ et al., 2002), but further analysis of the tick genes encoding CC-chemokine binding proteins can be performed by using genomic DNA that can be extracted from ixodid ticks by applying specific methods and conditions (Hill CA and Gutierrez, JA 2003), in particular for detecting any significant polymorphism in salivary gland proteins, as already demonstrated (Wang H et al., 1999). The genomic and protein sequences of these organisms is important for understanding their physiology and biology, therefore providing information useful for understanding the role of the proteins of the invention in host, parasite, and parasite-born pathogens relationships (Valenzuela JG, 2002b).

The biochemical and physiological characterization of the CC-chemokine binding activities described for protein homologous to ChBP-59 in the present invention can be performed by applying any of the technologies recently improved for the study of tick and tick-borne pathogens, such as two-dimensional gel electrophoresis (Madden RD et al., 2004) or RNA interference (Aljamali MN et al., 2003). Moreover, further studies can be performed to map the CC-chemokine recognition site on these proteins and the mechanisms of CC-chemokine antagonism (Seet BT et al., 2001; Beck CG et al., 2001; Burns JM et al., 2002; Webb LM et al., 2004) or to identify relevant post-translational modifications (Alarcon-Chaidez FJ et al., 2003).

Another aspect of the invention are fusion proteins comprising a ChBP-59 polypeptide as defined above operably linked to a heterologous domain, e.g., one or more amino acid sequences which may be chosen amongst the following: an extracellular domain of a membrane-bound protein, immunoglobulin constant regions (Fc region), multimerization domains, export signals, and tag sequences (such as the ones helping the purification by affinity: HA tag, Histidine tag, GST, FLAAG peptides, or MBP).

In the context of a fusion protein, the expression "operably linked" indicates that the ChBP-59 polypeptide and additional amino acid sequences are associated through peptide linkage(s), either directly or via spacer residues (e.g., a linker). In this manner, the fusion protein can be produced recombinantly, by direct expression in a host cell of a nucleic acid molecule encoding the same, as will be discussed below. Also, if needed, the additional amino acid sequences included in the fusion protein can be eliminated, either at the end of the production/purification process or in vivo, e.g., by means of an appropriate endo-/exopeptidase, as will be discussed below. The heterologous moiety may be operably linked to either the N- or the C-terminal portion of the ChBP-59 polypeptide.

The design of the moieties and/or linkers, as well methods and strategies for the construction, purification, detection, maturation, and use of fusion proteins are widely discussed in the literature (Nilsson J et al., 1997; "Applications of chimeric genes and hybrid proteins" Methods Enzymol. Vol. 326-328, Academic Press, 2000). In general, the heterologous sequences are intended to provide additional properties without impairing the therapeutic activity of the original protein (CC-chemokine binding, for example) in a significant manner. Examples of such additional properties are an easier purification procedure, a longer lasting half-life in body fluids, an additional binding moiety, the maturation by means of an endoproteolytic digestion, the stability during recombinant production, or extracellular localization. This latter feature is of particular importance for defining a specific group of fusion or chimeric proteins included in the above definition since it allows the polypeptides to be localized in the space where the isolation and purification of these polypeptides is facilitated, and where CC-chemokines are normally active.

The choice of one or more of these sequences to be fused to a ChBP-59 polypeptide is functional to specific use and/or purification protocol of said protein as recombinant protein.

For example, the activity of CHBP-59 was tested in the examples by means of a fusion protein including a histidine tag sequence facilitating both detection and purification of CHBP-59. These sequences can be chosen amongst the following three basic groups of heterologous sequences.

A first group of such sequences consists of sequences helping the secretion and the purification of the protein using recombinant DNA technologies, such as a signal peptide and export signals (Rapoport TA et al., 1996), or tag sequences helping the purification by affinity (HA tag, Histidine tag, GST, FLAG, or MBP).

A second group of heterologous sequences is represented by those allowing a better stability and bioactivity of the proteins.

A typical example of a strategy allowing a prolonged half-life of a protein is the fusion with human serum albumin, or with peptides and other modified sequences (e.g. by myristoylation) that allow the binding to circulating human serum albumin, that (Chuang VT et al., 2002; Graslund T et al., 1997; WO 01/77137). Alternatively, the additional sequence may help the targeting to specific localization, such as in the brain (WO 03/32913).

Another way to improve the stability of a recombinant protein when administered to a subject is to generate multimers of the protein by fusing domains isolated from other proteins that allows the formation or dimers, trimers, etc. Examples protein sequences allowing the multimerization of the polypeptides of the Invention are domains isolated from proteins such hCG (WO 97/30161), collagen X (WO 04/33486), C4BP (WO 04/20639), Erb proteins (WO 98/02540), or coiled coil peptides (WO 01/00814).

A well known example of such fusion proteins is represented by the constant/Fc region of human immunoglobulin proteins, allowing the dimerization common to human immunoglobulins. Different strategies for generating fusion protein comprising a therapeutic protein and an immunoglobulin fragment are disclosed in the literature (WO 91/08298; WO 96/08570; WO 93/22332; WO 04/085478; WO 01/03737; WO 02/66514). For example, the nucleic acid sequence encoding the mature CHBP-59 can be cloned in an expression vector fused to a nucleic acid sequence encoding the original CHBP-59 signal sequence (or any other appropriate signal /export sequence) at its 5' end, and the nucleic acid sequence encoding the constant region of human immunoglobulin lambda heavy chain IgG1 (NCBI Acc. No. CAA75302; segment 246-477) at its 3' end. The resulting vector can be used to transform a CHO or HEK293 host cell line and the clones stably expressing and secreting the recombinant fusion protein having CHBP-59 at the N-terminus and the IgG1 sequence at the C-terminus can be selected. This done then can be used for scaling up the production and for purifying the recombinant fusion protein from the culture medium. Alternatively, the position of the nucleic acid encoding the constant region of human immunoglobulin lambda heavy chain IgG1 and CHBP-59 can be inversed, and the resulting protein can be expressed and secreted using still the original signal sequence of CHBP-59, or any other appropriate signal/export sequence. Using these technology it can be also possible to generate heterodimers if two different constructs expressing one CHBP-59-Fc fusion protein and the other a different Fc-based fusion protein (for example another CC-chemokine antagonist) are coexpressed in the same host cell (WO 00/18932).

A further group of heterologous sequences is represented by those adding a further functional activity that can synergise or amplify the ones shown by CHBP-59. These sequences, which are expected to be either isolated from an extracellular domain of a membrane-bound protein (such as a CC-chemokine receptor) or to be present in a secreted protein, can be active as well as CC-chemokine antagonist, and in general should have an immunomodulatory activity.

As mentioned above, the additional sequence included in the fusion proteins may be eliminated, e.g., at the end of the production or purification process, or in vivo, if needed, e.g., by means of an appropriate endo-/exopeptidase. For example, the linker sequence included in the recombinant protein may present a recognition site for an endopeptidase (such as a caspase) that can be used to detach enzymatically the desired protein from the heterologous sequence either in vivo or in vitro. Alternatively, if the protein sequence to be expressed does not contain a starting methionine (for example, if the sequence encodes for only the mature sequence of the protein, without the signal peptide), a protein of the Invention can be expressed correctly in a host cell with a starting Methionine. This additional amino acid may be then either maintained in the resulting recombinant protein, or eliminated by means of an exopeptidase, such as Methionine Aminopeptidase, according to methods disclosed in the literature (Van Valkenburgh HA and Kahn RA, 2002; Ben-Bassat A, 1991).

Further variants or analogs of the polypeptides of the invention can be obtained in the form of peptide mimetics (also called peptidomimetics), in which the nature of peptide or polypeptide has been chemically modified at the level of amino acid side chains, of amino acid chirality, and/or of the peptide backbone. These alterations are intended to provide antagonists with improved purification, potency and/or pharmacokinetics features. For example, when the peptide is susceptible to cleavage by peptidases following injection into the subject is a problem, replacement of a particularly sensitive peptide bond with a non-ceavable peptide mimetic can provide a peptide more stable and thus more useful as a therapeutic. Similarly, the replacement of an L-amino acid residue is a standard way of rendering the peptide less sensitive to proteolysis, and finally more similar to organic compounds other than peptides. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4-dinitrophenyl. Many other modifications providing increased potency, prolonged activity, ease of purification, and/or increased half-life are known in the art (WO 02/10195; Villain M et al., 2001). Preferred alternative, "synonymous" groups for amino acid derivatives included in peptide mimetics are those defined in Table II. By "amino acid derivative" is intended an amino acid or amino acid-like chemical entity other than one of the 20 genetically encoded naturally occurring amino acids. In particular, the amino acid derivative may contain substituted or non-substituted alkyl moieties that can be linear, branched, or cyclic, and may include one or more heteroatoms. The amino acid derivatives can be made de novo or obtained from commercial sources (Calbiochem-Novabiochem AG, Switzerland; Bachem, USA). The techniques for the synthesis and the development of peptide mimetics, as well as non-peptide mimetics, are well known in the art (Hruby VJ and Balse PM, 2000; Golebiowski A et al., 2001). Various methodologies for incorporating unnatural amino acids into proteins, using both in vitro and in vivo translation systems, to probe and/or improve protein structure and function are also disclosed in the literature (Dougherty DA, 2000).

As will be discussed below, the polypeptides of the invention may be prepared by any procedure known in the art, including recombinant technologies and chemical synthesis technologies.

A further object of the invention resides in a nucleic acid molecule encoding a polypeptide as defined above, i.e., a polypeptide comprising the amino acid sequence of ChBP-59 or of a fragment or analog thereof. Particular a nucleic acid molecules of this invention are selected from the group consisting of:

a) a nucleic acid molecule encoding a protein comprising an amino acid sequence of ChBP-59 (SEQ ID NO: 5);
b) a nucleic acid molecule encoding a protein comprising an amino acid sequence of mature ChBP-59 (SEQ ID NO: 6);
c) a nucleic acid molecule encoding a protein comprising an amino acid sequence of ChBP-59-HIS (SEQ ID NO: 17);
d) a nucleic acid molecule encoding a protein comprising an amino acid sequence of mature ChBP-59-HIS (SEQ ID NO: 18);
e) a nucleic acid molecule capable of hybridization to a nucleic acid molecule of a), b), c) or d) under moderately stringent conditions, and which encodes a protein that binds a CC-chemokine;
f) a nucleic acid molecule encoding a protein at least about 70% identical in amino acid sequence to a protein of a), b), c), or d), and that binds a CC-chemokine;
g) a nucleic acid molecule encoding a protein comprising a fragment of a protein encoded by a nucleic acid molecule of a), b), c), d), e), or f), which fragment binds a CC-chemokine; and
h) a degenerate variant of a nucleic acid molecule of a), b), c), d), e), f) or g).

In particular, the nucleic acid molecule encodes a protein selected from the group consisting of:

a) a protein having an amino acid sequence of ChBP-59 (SEQ ID NO: 5);
b) a protein having an amino acid sequence of mature ChBP-59 (SEQ ID NO 6);
c) a protein having an amino acid sequence of ChBP-59-HIS (SEQ ID NO: 17);
d) a protein having an amino acid sequence of mature ChBP-59-HIS (SEQ ID NO: 18);
e) a protein comprising a fragment of a protein of a), b), c), or d), which fragment binds a CC-chemokine;
f) a protein comprising a fragment of a protein of a), b), c), or d), which fragment has an immunomodulatory activity;
g) an active mutant of a protein of a), b), c), or d), in which mutant one or more amino acid residues have been added, deleted, or substituted and which mutant binds a CC-chemokine; and
h) a fusion protein, which fusion protein comprises a protein of a), b), c), d), e), f), or g) operably linked to one or more amino acid sequences chosen amongst the following: an extracellular domain of a membrane-bound protein, an immunoglobulin constant region, a multimerization domain, a signal peptide, an export signal, and a tag sequence.

Within the context of the present invention, a "degenerate variant" designates all nucleic acid sequences that, by virtue of the degeneracy of the genetic code, code for the same amino acid sequence as a reference nucleic acid.

Furthermore, the term "nucleic acid molecule" encompasses all different types of nucleic acids, including without limitation deoxyribonucleic acids (e.g., DNA, cDNA, gDNA, synthetic DNA, etc.), ribonucleic acids (e.g., RNA, mRNA, etc.) and peptide nucleic acids (PNA). In a preferred embodiment, the nucleic acid molecule is a DNA molecule, such as a double-stranded DNA molecule, typically a cDNA.

If the main aspects are directed to the DNA and protein sequences of ChBP-59 disclosed in the examples, specific embodiments include a series of ChBP-59-related sequences, such as DNA or RNA sequences capable of hybridizing under moderately stringent conditions (prewashing solution of 5×SSC, 0.5% SDS, 1.0 mM EDTA (pH 8.0) and hybridization conditions of 50° C., 5×SSC, overnight) to the DNA sequences encoding ChBP-59, and that code for a CC-chemokine binding protein.

For example, the Invention provides the sequence of the cDNA of *Rhipicephalus sanguineus* expressing ChBP-59 (SEQ ID NO: 3), the associated Open Reading Frame (ORF; SEQ ID NO: 4), a modified cDNA sequence allowing the expression of ChBP-59 as a recombinant protein fused to an histidine tag in mammalian or insect host cells (SEQ ID NO: 15), and the associated ORF (SEQ ID NO: 16), In other preferred embodiments the ChBP-59-related sequences are DNA molecules encoding proteins that are at least about 70%, preferably 80%, and most preferably 90% identical in amino acid sequence to ChBP-59. This value can be calculated with any of the dedicated programs, such as FASTA (Pearson WR, 2000), and, for fragment or partial sequences, it is calculated on that portion of ChBP-59 that is present in the fragment.

Another preferred embodiment is an oligonucleotide that comprises a fragment of, or that hybridizes specifically to a region of the sequence of a nucleic acid molecule as defined above. Such oligonucleotides typically contain between 5 and 100 nucleotides in length, and can be selected e.g., from the group consisting of oligonucleotides of at least about 20 nucleotides in length, oligonucleotides of at least about 30 nucleotides in length, and oligonucleotides of at least about 50 nucleotides in length. These oligonucleotides can be used for detecting (by PCR or Southern blot, for example) the non-/coding sequences in transcripts encoding ChBP-59 and related sequences in a sample, or for generating and subcloning recombinant variants of ChBP-59, as shown in the example for the 3' end of the primers used for subcloning and modifying ChBP-59 coding sequence as a histidine tagged variant (59-attB1 forward and 59-attB2 reverse; SEQ ID NO: 7 and 8).

In a further aspect, the nucleic acid molecules defined above can be comprised in a cloning or expression vector. In this regard, a particular object of this invention resides in an expression vector comprising a promoter operably associated to a nucleic acid molecule as defined above, in particular a tissue specific, constitutive promoter or regulated (e.g., inducible) promoter. The vector may comprise any additional regulatory element, such as a terminator, enhancer, origin of replication, selection marker, etc. The vector may be a plasmid, cosmid, viral vector, phage, artificial chromosome, and the like.

In a particular embodiment, this vector can comprise:

a) a DNA of the invention; and
b) an expression cassette;

wherein said DNA (a) is operably associated with a tissue specific, a constitutive, or an inducible promoter included in sequence (b).

Optionally, if the coding nucleic acid (i.e., sequence (a)) does not contain a codon for a starting methionine (for example, if this sequence encodes for only the mature sequence of the protein, without the signal peptide) the vector or expression cassette may also contain an ATG sequence that is cloned in 5' to such sequence so that it can be expressed correctly with a starting Methionine. This additional amino acid may be then either maintained in the resulting recombinant protein, or eliminated by means of an enzyme, such as Methionine Aminopeptidase, according to methods disclosed in the literature (Van Valkenburgh HA and Kahn RA, 2002; Ben-Bassat A, 1991).

This vector may allow the expression of the proteins of the Invention not only in the condition of tissue culture but also in vivo, for either experimental or therapeutic reasons. For example, cells overexpressing the protein of the Invention can be transferred (e.g. encapsulated) in an animal model to check the physiological effects of the constant administration of the protein, and eventually before applying the cells to humans. Alternatively, the vector can be used for retrovirus-mediated gene transfer, or any other technology allowing the introduction and the expression of a vector or of the isolated DNA coding sequence in animal under the control of an endogenous promoter. This approach allows the generation of transgenic non-human animals in which the proteins of the Invention are expressed constitutively or in a regulated manner (e.g. in specific tissues and/or following the induction with specific compounds). Similar approaches were applied to other non-mammalian chemokine-binding protein, showing various developmental and pathological effects (Jensen KK et al., 2003; Pyo R et al., 2004; Bursill CA et al., 2004).

Another object of the Invention are host cells transformed or transfected with a cloning or expression vector above indicated. These vectors can be used in a process of preparation of the polypeptides of the Invention. In this respect, an object of the invention is a method of preparing a ChBP-598 polypeptide as defined above, comprising culturing recombinant cells as defined above under conditions allowing or promoting expression and recovering the ChBP-59 polypeptide. When the vector expresses the polypeptide as a protein secreted in the extracellular space, the protein can be more easily collected and purified from cultured cells in view of further processing.

Many books and reviews provides teachings on how to clone and produce recombinant proteins using vectors and Prokaryotic or Eukaryotic host cells, such as some titles in the series "A Practical Approach" published by Oxford University Press ("DNA Cloning 2: Expression Systems", 1995; "DNA Cloning 4: Mammalian Systems", 1996; "Protein Expression", 1999; "Protein Purification Techniques", 2001). In particular, the examples show how, once that the DNA sequence encoding for ChBP-59 has been identified by screening the *Rhipicephalus sanguineus* cDNA library, the ORF can be adapted, modified, and inserted into expression vectors for obtaining the corresponding recombinant protein.

In general, the vectors can be episomal or non-/homologously integrating vectors, which can be introduced in the appropriate host cells by any suitable means (transformation, transfection, conjugation, protoplast fusion, electroporation, calcium phosphate-precipitation, direct microinjection, etc.) to transform them. Factors of importance in selecting a particular plasmid, viral, or retroviral vector include: the ease with which recipient cells that contain the vector, may be recognized and selected from those recipient cells which do not contain the vector; the number of copies of the vector which are desired in a particular host; and whether it is desirable to be able to "shuttle" the vector between host cells of different species. The vectors should allow the expression of the isolated proteins of the invention, or the fusion proteins comprising them in the prokaryotic or Eukaryotic host cell under the control of appropriate transcriptional initiation/termination regulatory sequences, which are chosen to be constitutively active or inducible in said cell. A cell line substantially enriched in such cells can be then isolated to provide a stable cell line (as shown in the example with HEK293 and TN5 cell lines).

For Eukaryotic host cells (e.g. yeasts, insect or mammalian cells), different transcriptional and translational regulatory sequences may be employed, depending on the nature of the host. They may be derived form viral sources, such as adenovirus, bovine papilloma virus, Simian virus or the like, where the regulatory signals are associated with a particular gene which has a high level of expression. Examples are the TK promoter of the Herpes virus, the SV40 early promoter, the yeast gal4 gene promoter, etc. Transcriptional initiation regulatory signals may be selected which allow for repression and activation, so that expression of the genes can be modulated. The cells which have been stably transformed by the introduced DNA can be selected by also introducing one or more markers which allow for selection of host cells which contain the expression vector. The marker may also provide for phototrophy to an auxotropic host, biocide resistance, e.g. antibiotics, or heavy metals such as copper, or the like. The selectable marker gene can either be directly linked to the DNA gene sequences to be expressed, or introduced into the same cell by co-transfection. Additional elements may also be needed for optimal synthesis of proteins of the invention.

Host cells for recombinant production may be either Prokaryotic or Eukaryotic cells. Particularly suitable Prokaryotic cells include bacteria (such as *Bacillus subtilis* or *E. coli*) transformed with a recombinant bacteriophage, plasmid or cosmid DNA expression vectors. Preferred are Eukaryotic host cells, e.g. mammalian cells, such as human, monkey, mouse, and Chinese Hamster Ovary (CHO) cells, because they provide post-translational modifications to protein molecules, including correct folding or glycosylation at correct sites. Alternative Eukaryotic host cells are yeast cells transformed with yeast expression vectors Also yeast cells can carry out post-translational peptide modifications including glycosylation. A number of recombinant DNA strategies exist which utilize strong promoter sequences and high copy number of plasmids that can be utilized for production of the desired proteins in yeast. Yeast recognizes leader sequences in cloned mammalian gene products and secretes peptides bearing leader sequences (i.e., pre-peptides).

For long-term, high-yield production of a recombinant polypeptide, stable expression is preferred. For example, cell lines which stably express the polypeptide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type. A cell line substantially enriched in such cells can be then isolated to provide a stable cell line.

A particularly preferred method of high-yield production of a recombinant polypeptide of the present invention is through the use of dihydrofolate reductase (DHFR) amplification in DHFR-deficient CHO cells, by the use of successively increasing levels of methotrexate as described in U.S. Pat. No. 4,889,803. The polypeptide obtained may be in a glycosylated form.

Mammalian cell lines available as hosts for expression are known in the art and include many immortalised cell lines available from the American Type Culture Collection (ATCC) including, but not limited to, Chinese hamster ovary (CHO), HeLa, baby hamster kidney (BHK), monkey kidney (COS), C127, 3T3, BHK, HEK 293, Bowes melanoma and human hepatocellular carcinoma (for example Hep G2) cells and a number of other cell lines. In the baculovirus system, the materials for baculovirus/insect cell expression systems are commercially available in kit form from, inter alia, Invitrogen.

Alternatively, the polypeptides of this invention may be prepared by artificial synthesis. In this regard, examples of chemical synthesis technologies are solid phase synthesis and liquid phase synthesis. As a solid phase synthesis, for example, the amino acid corresponding to the carboxy-terminus of the peptide to be synthetised is bound to a support which is insoluble in organic solvents, and by alternate repetition of reactions, one wherein amino acids with their amino groups and side chain functional groups protected with appropriate protective groups are condensed one by one in order from the carboxy-terminus to the amino-terminus, and one where the amino acids bound to the resin or the protective group of the amino groups of the peptides are released, the peptide chain is thus extended in this manner. Solid phase synthesis methods are largely classified by the tBoc method and the Fmoc method, depending on the type of protective group used. Typically used protective groups include tBoc t-butoxycarbonyl), Cl-Z (2-chlorobenzyloxycarbonyl), Br-Z (2-bromobenzyloxycarbonyl), Bzl (benzyl), Fmoc (9-fluorenylmethoxycarbonyl), Mbh (4,4'-dimethoxydibenzhydryl), Mtr (4-methoxy-2,3,6-trimethylbenzenesulphonyl), Trt (trityl), Tos (tosyl), Z (benzyloxycarbonyl) and C12-Bzl (2,6-dichlorobenzyl) for the amino groups; NO2 (nitro) and Pmc (2,2,5,7,8-pentamethylchromane-6-sulphonyl) for the guanidino groups); and tBu (t-butyl) for the hydroxyl groups). After synthesis of the desired polypeptide, it is subjected to the de-protection reaction and cut off from the solid support. Such peptide cutting reaction may be carried with hydrogen fluoride or tri-fluoromethane sulfonic acid for the Boc method, and with TFA for the Fmoc method. Totally synthetic proteins of size comparable to that of ChBP-59 are disclosed in the literature (Brown A et al., 1996).

The polypeptides of the present invention can be produced, formulated, administered, or generically used in other alternative forms that can be preferred according to the desired method of use and/or production. The protein of the invention can be post-translationally modified, for example by glycosylation as shown in the examples.

In general the protein of the invention can be provided in the form of active fractions, precursors, salts, derivatives, conjugates or complexes.

As indicated above, the term "active" or "biologically active" means that such alternative compounds should maintain, or even potentiate, the CC-chemokine binding and/or immunomodulatory properties of ChBP-59.

The term "fraction" refers to any fragment of the polypeptidic chain of the compound itself, alone or in combination with related molecules or residues bound to it, for example residues of sugars or phosphates. Such molecules can result also from other modifications that do not normally alter primary sequence, for example in vitro chemical derivatization of peptides (acetylation or carboxylation), and those made by modifying the protein post-translationally, such as by phosphorylation (introduction of phosphotyrosine, phosphoserine, or phosphothreonine residues) or by glycosylation (by exposing the peptide to enzymes which affect glycosylation e.g., mammalian glycosylating or deglycosylating enzymes) during its synthesis and/or in further processing steps. In particular, ChBP-59 has been characterized in tick saliva and in both recombinant forms disclosed herein as being more or less heavily glycosylated. This modification may be performed in vitro, by using the appropriate modifying enzyme, or in vitro, by choosing the appropriate host cells for recombinant production.

The "precursors" are compounds which can be converted into the compounds of present invention by metabolic and enzymatic processing prior or after the administration to the cells or to the body.

The term "salts" herein refers to both salts of carboxyl groups and to acid addition salts of amino groups of the peptides, polypeptides, or analogs thereof, of the present invention. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid. Any of such salts should have substantially similar activity to the peptides and polypeptides of the invention or their analogs.

The term "derivatives" as used herein refers to derivatives that can be prepared from the functional groups present on the lateral chains of the amino acid moieties or on the amino-/ or carboxy-terminal groups according to known methods. Such derivatives include for example esters or aliphatic amides of the carboxyl-groups and N-acyl derivatives of free amino groups or O-acyl derivatives of free hydroxyl-groups and are formed with acyl-groups as for example alcanoyl- or aroyl-groups.

The proteins of the Invention can be in the form of active conjugate or complex with a molecule chosen amongst radioactive labels, biotin, fluorescent labels, cytotoxic agents, and drug delivery agents. Useful conjugates or complexes can be generated, using molecules and methods known in the art, for various reasons, for example for allowing the detection of the interaction with CC-chemokines or other proteins (radioactive or fluorescent labels, biotin), therapeutic efficacy (cytotoxic agents), or improving the agents in terms of drug delivery efficacy, such as polyethylene glycol and other natural or synthetic polymers (Harris JM and Chess RB, 2003; Greenwald RB et al., 2003; Pillai O and Panchagnula R, 2001).

These ChBP-59-derived compounds may be produced following a site-directed modification of an appropriate residue, in an internal or terminal position. Residues can be used for attachment, provided they have a side-chain amenable for polymer attachment (i.e., the side chain of an amino acid bearing a functional group, e.g., lysine, aspartic acid, glutamic acid, cysteine, histidine, etc.). Alternatively, a residue at these sites can be replaced with a different amino acid having a side chain amenable for polymer attachment.

For example, an additional Cysteine allowing direct PEGylation can be added at the N- or C-terminus of the mature protein sequence by recombinant DNA technologies or enzimatically. Alternatively, the Cysteine may be included in the protein by the substitution of a residue, for example in correspondence of a glycosylation site.

Moreover, the side chains of the genetically encoded amino acids can be chemically modified for polymer attachment, or unnatural amino acids with appropriate side chain functional groups can be employed. Polymer attachment may be not only to the side chain of the amino acid naturally occurring in a specific position of the antagonist or to the side chain of a natural or unnatural amino acid that replaces the amino acid naturally occurring in a specific position of the antagonist, but also to a carbohydrate or other moiety that is attached to the side chain of the amino acid at the target position.

Polymers suitable for these purposes are biocompatible, namely, they are non-toxic to biological systems, and many such polymers are known. Such polymers may be hydrophobic or hydrophilic in nature, biodegradable, non-biodegradable, or a combination thereof. These polymers include natural polymers (such as collagen, gelatin, cellulose, hyaluronic acid), as well as synthetic polymers (such as polyesters, polyorthoesters, polyanhydrides). Examples of hydrophobic non-degradable polymers include polydimethyl siloxanes, polyurethanes, polytetrafluoroethylenes, polyethylenes, polyvinyl chlorides, and polymethyl methaerylates. Examples of hydrophilic non-degradable polymers include poly(2-hydroxyethyl methacrylate), polyvinyl alcohol, poly (N-vinyl pyrrolidone), polyalkylenes, polyacrylamide, and copolymers thereof. Preferred polymers comprise as a sequential repeat unit ethylene oxide, such as polyethylene glycol (PEG).

The preferred method of attachment employs a combination of peptide synthesis and chemical ligation. Advantageously, the attachment of a water-soluble polymer will be through a biodegradable linker, especially at the amino-terminal region of a protein. Such modification acts to provide the protein in a precursor (or "pro-drug") form, that, upon degradation of the linker releases the protein without polymer modification.

In another aspect the present invention relates to antibodies that selectively bind the proteins of the invention.

The term "antibody" as used herein encompasses monoclonal and polyclonal antibodies, chimeric, humanized, fully human, bispecific or multispecific antibodies as well as fragments thereof such as single chain antibodies (scFv) or domain antibodies, as further explained below.

Within the context of this invention, the term "selective" binding indicates that the antibodies preferentially bind the target polypeptide or epitope, i.e., with a higher affinity than any binding to any other antigen or epitope. In other words, binding to the target polypeptide can be discriminated from non-specific binding to other antigens. It is preferred that the antibodies according to the present invention exhibit binding affinity (Ka) to the target polypeptide or epitope of $10^6$ $M^{-1}$ or greater, preferably $10^7$ $M^{-1}$ or greater, more preferably $10^8$ $M^{-1}$ or greater and most preferably $10^9$ $M^{-1}$ or greater. The binding affinity of an antibody can be readily determined by one of ordinary skill in the art, for example, by Scatchard analysis (Scatchard G., 1949).

Antibodies of this invention may be monoclonal or polyclonal antibodies, or fragments or derivative thereof having substantially the same antigen specificity.

Methods of preparing polyclonal antibodies from various species, including rodents, primates and horses, have been described for instance in Vaitukaitis et al (1971). Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the polypeptide of SEQ ID NO 5, 6, 17, 18 or a variant as described hereabove or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). Repeated injections may be performed. Blood samples are collected and immunoglobulins or serum are separated.

The antibodies may, alternatively, be monoclonal antibodies. The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. The modifier "monoclonal" indicates the character of the antibody as being obtained from a substantially homogeneous population of antibodies, and is not to be construed as requiring production of the antibody by any particular method.

Methods of producing monoclonal antibodies may be found, for instance, in Kohler et al (Nature 256 (1975) 495), incorporated therein by reference.

In a hybridoma method, a mouse, hamster, or other appropriate host animal, is typically immunized with an immunizing agent (the immunizing agent will typically include the polypeptide of SEQ ID NO: 5, 6, 17, 18 or a variant as described hereabove or a fusion protein thereof) to elicit lymphocytes that produce or are capable of producing antibodies that will specifically bind to the immunizing agent. Alternatively, the lymphocytes may be immunized in vitro. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding 1986). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells. Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies.

The culture medium in which the hybridoma cells are cultured can then be assayed for the presence of monoclonal antibodies directed against the immunizing peptide. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art.

After the desired hybridoma cells are identified, the clones may be subcloned by limiting dilution procedures and grown by standard methods (Goding, supra). Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells.

The "monoclonal antibodies" may also be isolated from phage antibody libraries using the techniques described in Clackson et al., 1991 and Marks et al, 1991.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

Antibodies may also be produced by selection of combinatorial libraries of immunoglobulins, as disclosed for instance in Ward et al (1989).

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of non-human species (donor antibody) such as mouse, rat or rabbit having the desired specificity, affinity and capacity. In some instances, Fv framework residues of the human immunoglobulin are replaced by corresponding non-human residues.

Methods for humanizing non-human antibodies are well known in the art. Humanization can be essentially performed following the method of Winter and co-workers (Jones et al., Nature, 321:522-525 (1986)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species.

Human antibodies can also be produced using various techniques known in the art, including phage display libraries (Hoogenboom and Winter, (1991). Similarly, human antibodies can be made by the introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625, 126; 5,633,425; 5,661,016

The invention also pertains to immunoconjugates comprising an antibody conjugated to heterologous moieties, such as cytotoxic agents, labels, drugs or other therapeutic agents, covalently bound or not, either directly or through the use of coupling agents or linkers. Cytotoxic agent include chemotherapeutic agent, toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

In another embodiment, the antibody may be conjugated to a "receptor" (such as streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

Moreover, antibodies or antibody fragments of the present invention can be PEGylated using methods in the art and described herein. The antibodies disclosed herein may also be formulated as immunoliposomes. Liposomes with enhanced circulation time are disclosed in U.S. Pat. No. 5,013,556.

The invention also pertains to "Antibody fragments" which comprise a portion of an intact antibody, preferably the antigen binding or variable region of the intact antibody. Examples of antibody fragments include Fab, Fab', F(ab')2, and Fv fragments; diabodies; linear antibodies; single-chain antibody molecules; monobodies; diabodies; camelized monobodies; domain antibodies and multispecific antibodies formed from antibody fragments.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known. The "light chains" of antibodies (immunoglobulins) from any vertebrate species can be assigned to one of two clearly distinct types, called kappa and lambda, based on the amino acid sequences of their constant domains.

"Single-chain antibody molecules" are fragments of an antibody comprising the VH and VL domains of said antibody, wherein these domains are present in a single polypeptide chain. Preferably, the Fv polypeptide further comprises a polypeptide linker between the VH and VL domains which enables the single-chain antibody molecule to form the desired structure for antigen binding.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161.

The term "monobody" as used herein, refers to an antigen binding molecule with a heavy chain variable domain and no light chain variable domain. A monobody can bind to an antigen in the absence of light chains and typically has three CDR regions designated CDRH1, CDRH2 and CDRH3. A heavy chain IgG monobody has two heavy chain antigen binding molecules connected by a disulfide bond. The heavy chain variable domain comprises one or more CDR regions, preferably a CDRH3 region.

A "camelized monobody" refers to a monobody or antigen binding portion thereof obtained from a source animal of the camelid family, including animals with feet with two toes and leathery soles. Animals in the camelid family include camels, llamas, to and alpacas. It has been reported that camels (Camelus dromedaries and Camelus bactrianus) often lack variable light chain domains when IgG-like material from their serum is analyzed, suggesting that sufficient antibody specificity and affinity can be derived from VH domains (three CDR loops) alone.

Also included into the invention are single domain antibodies. Single domain antibodies, also called domain antibodies or dAbs, are the smallest functional binding units of antibodies, corresponding to the variable regions of either the heavy (VH) or light (VL) chains of human antibodies. Domain antibodies have a molecular weight of approximately 13 kDa, or less than one-tenth the size of a full antibody. In contrast to conventional antibodies, domain antibodies are well expressed in bacterial, yeast, and mammalian cell systems. In addition, many domain antibodies are highly stable and retain activity even after being subjected to harsh conditions, such as freeze-drying or heat denaturation which makes them amenable to a wide range of pharmaceutical formulation conditions and manufacture processes.

The proteins of the invention can be provided in more or less purified forms. The examples show how to clone nucleic acids necessary for expressing recombinant ChBP-59, how to purify recombinant or natural ChBP-59 using the affinity for CC-chemokines and chromatographic technologies, and how to select cells properly expressing this protein by means of assays for detecting CC-chemokine binding activities.

In particular, purification of the natural, synthetic or recombinant antagonists of the invention can be carried out by any one of the methods known for this purpose, i.e. any conventional procedure involving extraction, precipitation, chromatography, electrophoresis, or the like. A further purification procedure that may be used in preference for purifying the protein of the invention is affinity chromatography using monoclonal antibodies or affinity groups, which bind the target protein and which are produced and immobilized on a gel matrix contained within a column. Impure preparations containing the proteins are passed through the column. The protein will be bound to the column by heparin or by the specific antibody while the impurities will pass through. After washing, the protein is eluted from the gel by a change in pH or ionic strength. Alternatively, HPLC (High Performance Liquid Chromatography) can be used. The elution can be carried using a water-acetonitrile-based solvent commonly employed for protein purification. Purified preparations of the proteins of the Invention, as used herein, refers to the preparations which are at least 1% (by dry weight), and preferably at least 5%, of said proteins.

Another aspect of the present invention is a pharmaceutical composition comprising a ChBP-59 polypeptide as defined above (in the form of proteins and their alternative forms described above) as active ingredient, and a suitable diluent or carrier.

Another aspect of the present invention is a pharmaceutical composition comprising a nucleic acid molecule encoding a ChBP-59 polypeptide as defined above, or a corresponding vector or recombinant host cell, and a suitable diluent or carrier.

A further aspect of this invention relates to the use of a ChBP-59 polypeptide as defined above, or a nucleic acid encoding the same, for the manufacture of a medicament for use in regulating an immune response in a subject.

These compositions can be used as medicaments, in particular, for regulating an immune or inflammatory response in a mammal, and more particularly as anti-inflammatory compounds.

In general, given the involvement of CC-chemokines in many human and veterinary disorders, the CC-chemokine binding proteins of the invention can used as antagonists of CC-chemokine (such as CCL5/RANTES, CCL3/MIP-1 alpha, or CCL2/MCP-1) for the treatment or prevention of CC-chemokine-related disorders in animals. A non-exhaustive list of CC-chemokine-related disorders includes: inflammatory diseases, autoimmune diseases, immune diseases, infections, allergic diseases, cardiovascular diseases, metabolic diseases, gastrointestinal diseases, neurological diseases, sepsis, diseases related to transplant rejection, or fibrotic diseases. Non-limiting examples of these diseases are the following: arthritis, rheumatoid arthritis (RA), psoriatic arthritis, psoriasis, rheumatoid arthritis, restenosis, sepsis, osteoarthritis, systemic lupus erythematosus (SLE), systemic sclerosis, scleroderma, polymyositis, glomerulonephritis, fibrosis, allergic or hypersensitvity diseases, dermatitis, asthma, chronic obstructive pulmonary disease (COPD), inflammatory bowel disease (IBD), Crohn's diseases, fibromas, ulcerative colitis, multiple sclerosis, septic shock, viral infection, cancer, endometriosis, transplantation, graft-versus-host disease (GVHD) cardiac and renal reperfusion injury, ischemia and atherosclerosis.

The proteins of the invention, or specific fragments, can be used as active ingredients in the manufacture of pharmaceutical compositions for regulating an immune or inflammatory response in a mammal, for example of anti-inflammatory compositions. Alternatively, the proteins of the invention, or specific fragments, can be used as active ingredients in the manufacture of pharmaceutical compositions for the vaccination of a mammal against parasites, virus, or bacteria. The process for the preparation of such pharmaceutical compositions comprises combining ChBP-59 together with a pharmaceutically acceptable diluent or carrier.

A pharmaceutical composition containing a protein of the invention as active ingredient can be used for binding a CC-chemokine in vivo, blocking the binding of a CC-chemokine to a corresponding cell surface receptor and consequently producing a potentially therapeutic effect, such as an anti-inflammatory effect. A pharmaceutical composition containing a protein of the invention as active ingredient, can be used also for binding to CC-chemokine analogues present in viruses, bacteria, or parasites to block entry of said virus, bacteria, or parasite into cells. Pharmaceutical compositions for vaccination of a mammal against a parasite, a virus or a bacteria, can comprise a fragment of the protein of the invention as active ingredient. The compositions above indicated can further comprise an additional immunosuppressant or anti-inflammatory substance.

The pharmaceutical compositions may contain, in combination with the proteins of the invention as active ingredient, suitable pharmaceutically acceptable diluents, carriers, biologically compatible vehicles and additives which are suitable for administration to an animal (for example, physiological saline solution) and eventually comprising auxiliaries (like excipients, stabilizers, or adjuvants) which facilitate the processing of the active compounds into preparations which can be used pharmaceutically. The pharmaceutical compositions may be formulated in any acceptable way to meet the needs of the mode of administration. For example, the use of biomaterials and other polymers for drug delivery, as well the different techniques and models to validate a specific mode of administration, are disclosed in literature (Luo B and Prestwich GD, 2001; Cleland JL et al., 2001).

"Pharmaceutically acceptable" is meant to encompass any carrier, which does not interfere with the effectiveness of the biological activity of the active ingredient and that is not toxic to the host to which is administered. For example, for parenteral administration, the above active ingredients may be formulated in unit dosage form for injection in vehicles such as saline, dextrose solution, serum albumin and Ringer's solution. Carriers can be selected also from starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the various oils, including those of petroleum, animal, vegetable or synthetic origin (peanut oil, soybean oil, mineral oil, sesame oil).

Any accepted mode of administration can be used and determined by those skilled in the art to establish the desired blood levels of the active ingredients. For example, administration may be by various parenteral routes such as subcutaneous, intravenous, intradermal, intramuscular, intraperitoneal, intranasal, transdermal, rectal, oral, or buccal routes. The pharmaceutical compositions of the present invention can also be administered in sustained or controlled release dosage forms, including depot injections, osmotic pumps, and the like, for the prolonged administration of the polypeptide at a predetermined rate, preferably in unit dosage forms suitable for single administration of precise dosages.

Parenteral administration can be by bolus injection or by gradual perfusion over time. Preparations for parenteral administration include sterile aqueous or non-aqueous solutions, suspensions, and emulsions, which may contain auxiliary agents or excipients known in the art, and can be prepared according to routine methods. In addition, suspension of the active compounds as appropriate oily injection suspensions may be administered. Suitable lipophilic solvents or vehicles include fatty oils, for example, sesame oil, or synthetic fatty acid esters, for example, sesame oil, or synthetic fatty acid esters, for example, ethyl oleate or triglycerides. Aqueous injection suspensions that may contain substances increasing the viscosity of the suspension include, for example, sodium carboxymethyl cellulose, sorbitol, and/or dextran. Optionally, the suspension may also contain stabilizers. Pharmaceutical compositions include suitable solutions for administration by injection, and contain from about 0.01 to 99.99 percent, preferably from about 20 to 75 percent of active compound together with the excipient.

It is understood that the dosage administered will be dependent upon the age, sex, health, and weight of the recipient, kind of concurrent treatment, if any, frequency of treatment, and the nature of the effect desired. The dosage will be tailored to the individual subject, as is understood and determinable by one of skill in the art. The total dose required for each treatment may be administered by multiple doses or in a single dose. The pharmaceutical composition of the present invention may be administered alone or in conjunction with other therapeutics directed to the condition, or directed to other symptoms of the condition. Usually a daily dosage of active ingredient is comprised between 0.01 to 100 milligrams per kilogram of body weight per day. Ordinarily 1 to 40 milligrams per kilogram per day given in divided doses or in sustained release form is effective to obtain the desired results. Second or subsequent administrations can be performed at a dosage, which is the same, less than, or greater than the initial or previous dose administered to the individual.

Another aspect of the invention is the use of a protein encoded by a DNA of the Invention as a medicament, in particular in the preparation of a composition for regulating an immune or inflammatory response in a mammal.

Further aspects of the Invention are methods for immunising an animal against a blood-feeding ectoparasite, or for regulating an immune or inflammatory response in an animal in need thereof, comprising administering to said animal with a protein of the Invention said animal for a time and under conditions sufficient to regulate said immune response.

Another object of the invention is a method for treating or preventing CC-chemokine-related diseases comprising the administration of an effective amount of the compounds of the present invention.

An "effective amount" refers to an amount of the active ingredients that is sufficient to affect the course and the severity of the disease, leading to the reduction or remission of such pathology. The effective amount will depend on the route of administration and the condition of the patient.

The wording "CC-chemokine-related diseases" indicate any disease due to an excessive or uncontrolled CC-chemokine production, leading to a massive monocyte/macrophage/neutrophil/T-cell infiltration, and wherein the administration of ChBP-59 may provide a beneficial effect. A non-exhaustive list of such chronic, acute, or inherited diseases is provided above.

The therapeutic applications of the CC-chemokine antagonists of the invention and of the related reagents can be evaluated (in terms or safety, pharmacokinetics and efficacy) by the means of the in vivo or in vitro assays making use of mammalian cells, tissues and models (Coleman R et al., 2001; Li A, 2001; Methods Mol. Biol vol. 138, "Chemokines Protocols", edited by Proudfoot A et al., Humana Press Inc., 2000; Methods Enzymol, vol. 287 and 288, Academic Press, 1997). A non-limiting list of assays includes: calcium mobilisation, degranulation, upregulation of pro-inflammatory cytokines, upregulation of proteases, inhibition of cellular recruitment in vitro and in vivo.

Further aspect of the invention are test kits containing any of the compound disclosed in association to the CC-chemokine binding proteins of the invention. For example, a kit for detecting a CC-chemokine or an analogue, a CC-chemokine binding protein or a receptor, the interaction of CC-chemokine and a CC-chemokine binding protein, or antagonists or agonists of said interaction, comprising a detecting reagent and at least a compound selected from the group consisting of:

a) A nucleic acid molecule (e.g., a DNA);
b) An oligonucleotide;
c) A protein; and
d) An antibody;

derived from the CC-chemokine binding protein of the Invention.

These kits can be used in methods applicable in vitro or in vivo in which a sample is contacted by one of these compound, which can be labeled or immobilized on a solid support.

The present invention has been described with reference to the specific embodiments, but the content of the description comprises all modifications and substitutions, which can be brought by a person skilled in the art without extending beyond the meaning and purpose of the claims.

The invention will now be described by means of the following Examples, which should not be construed as in any way limiting the present invention. The Examples will refer to the Figures specified herein above.

EXAMPLES

Example 1

Screening of the *Rhipicephalus sanguineus* Saliva and cDNA Library for CC-Chemokine Binding Activities and Cloning of ChBP-59

Materials and Methods a. Screening of Chemokine-binding Activities in the Saliva of *Rhipicephalus sanguineus* (Common Brown Dog Tick)

Crude *Rhipicephalus sanguineus* tick saliva was obtained according to the protocol as published (Ferreira BR and Silva JS, 1998). Aliquots of *Rhipicephalus sanguineus* saliva (RSs) were tested using different assays including, as negative control, Bovine Serum Albumin (BSA) and, as positive control, a CC-chemokine-binding protein from ectromelia virus (known as vCCI or p35).

Different amounts of RSs and of vCCI were spotted onto nitrocellulose filters in parallel, and the filters exposed to different radiolabeled, recombinant CC- and CXC-chemokines.

A Scintillation Proximity Assay (SPA) was designed for detecting molecules interfering with the chemokine/chemokine receptor interaction as described in the literature (Alouani S, 2000). Briefly, wheat germ agglutinin SPA beads were coated with cell membranes isolated from CHO cell strains stably expressing a specific chemoine receptor (e.g. CCR1 or CCR5) and then incubated with the corresponding radiolabeled CC-chemokine alone, or in combination with the CC-chemokine.

b. Construction of the *Rhipicephalus sanguineus* cDNA Library and of the Control Plasmid Expressing vCCI Salivary glands were harvested from 100 adult ticks (*Rhipicephalus sanguineus*) and were immediately stored in ice-cold RNAlater™ solution (Ambion) until further use. Total RNA was extracted using the TRIzol™ method (Invitrogen) according to the manufacturer's instructions. The cDNA library was constructed in the phagemid vector λTriplEX2 using the SMART cDNA library construction kit (Clontech). The cDNAs were size-fractionated with a ChromaSpin 400 column (Clontech) according to the manufacturer's instructions before ligation to the vector. The size of the cloned cDNA inserts in the library ranged from about 0.6 kb to 1.5 kb and the frequency of inserts was approximately 80%.

The cDNA inserts from the *Rhipicephalus sanguineus* salivary gland cDNA library in pTriplEX2 were excised with restriction enzyme SfiI, and subcloned into the mammalian cell expression vector pEXP-lib (Clontech). The pEXP-Lib vector contains an expression cassette comprising the human cytomegalovirus (CMV) major immediate early promoter/enhancer followed by a multiple cloning site; an internal ribosome entry site (IRES) of the encephalomyocarditis virus (ECMV); a gene encoding puromycin resistance (puromycin-N-acetyl-transferase); and the polyadenylation signal of the bovine growth hormone. The multiple cloning site contains two distinct Sfi I sites (Sfi IA and Sfi IB, that differ in their interpalindromic sequences), which allows the directional subcloning of cDNA inserts from the pTriplEX2 vector to pEXPII.

The control protein vCCI (NCBI Acc. no. CAC05575; SEQ ID NO: 1) was expressed by cloning the cDNA encoding the protein (NCBI Acc. no. AJ277111; SEQ ID NO: 2) into pEXP-lib as described above to generate pEXP-lib vCCI.

c. Library Screening Using HEK293 Cells Supernatants

Human embryonic kidney cells 293 (HEK293 cells; ATCC Cat. No. CRC-1573) were maintained in DMEM-F12 Nut Mix, 10% heat-inactivated fetal calf serum, 2 mM L-Glutamine, 100 units/ml penicillin-streptomycin solution.

The pEXP-lib plasmids expressing *Rhipicephalus sanguineus* cDNA library were grouped into pools that were transfected into HEK293 cells using a GenePorter2 transfection kit (Gene Therapy Systems) according to the manufacturer's protocol. The pEXP-lib plasmid expressing the control protein vCCI was as well transfected in HEK293 in the same manner.

Culture medium from transfected HEK293 cells was harvested from cells grown in complete medium after three days in culture. The conditioned medium was centrifuged to remove cell debris, and the supernatant used in a crosslinking or SPA assay.

For crosslinking experiments media samples were transferred to a flat-bottom 96-well plate (Costar). A radiolabeled CC-chemokine ($^{125}$I-CCL3/MIP-1 alpha) was added to a final concentration of 0.23 nM to 50 µl of each sample of supernatant, which was then incubated with shaking for 2 hours at room temperature. A 25 µl aliquot from each well was then transferred to a new well containing 5 µl of 50 mM BS3 (crosslinking reagent) and further incubated for 2 hours with shaking. After this time 5 µl of 10×sample buffer (125 mM Tris base, pH 6.8, containing 10% SDS, 5 mM EDTA, 20% glycerol, 0.2% w/w bromophenol blue, 1 M DTT) were added to each well to stop the crosslinking reaction. The samples were then boiled for 5 minutes and electrophoresed on a 10% Bis-Tris SDS-polyacrylamide gel (Invitrogen NuPAGE, catalog no. NP0301 BOX). After electrophoresis the gel was sealed in Saran Wrap™ and exposed to a K-type storage phosphoimaging screen (Biorad) for 8 hours. Imaging screens were scanned at a resolution of 100 µm using a Biorad Personal FX phosphoimager.

Results

The saliva of the tick *Rhipicephalus sanguineus* has been already used to characterize immunomodulating activities, such as suppression of IgG and cytokine production (Matsumoto K et al., 2003) or T cell proliferation (Ferreira BR and Silva JS, 1998), but not activities directed specifically to CC-chemokines.

A CC-chemokine specific binding activity, comparable to the one detected using vCCI, a CC-chemokine-binding protein from ectromelia virus also known as p35 (Burns JM et al., 2002), was detected in the saliva of *Rhipicephalus sanguineus* by using both nitrocellulose filters spotted with the saliva and exposed to different radiolabeled CC-/CXC-chemokines, and a Scintillation Proximity Assay (SPA), a highthrouput screening technology allowing the measurement of molecular interactions with great precision.

The CC-chemokine binding activity was then identified in *Rhipicephalus sanguineus* at the DNA/protein sequence level in a cDNA library generated from *Rhipicephalus sanguineus* salivary glands. Pools of the cDNAs from this library were used to transfect mammalian cells (HEK293).

The clones expressing the transfected cDNAs encoding for a signal peptide-containing polypeptide secrete the protein into the culture medium. The supernatants have been tested directly, at different dilution, either in the SPA assay described above or in a crosslinking assay using a radiolabeled CC-chemokine ($^{125}$I-CCL3/MIP-1alpha). In particular, the addition of the crosslinking reagent to the radiolabeled CC-chemokine/CC-chemokine binding protein stabilizes the protein complex by linking the two molecules covalently. The resulting complex can be identified by SDS-polyacrylamide gel electrophoresis (SDS-PAGE) and subsequent autoradiography as a shifted band. This cross-linking method is very sensitive as nanogram amounts of protein can be detected.

The assays were performed by comparing the signal obtained with the supernatant obtained from the clone expressing the protein taken as positive control (vCCI), a supernatant in which recombinant vCCI was added, and a supernatant of non-transfected cells.

The pools of transfected HEK293 clones showing the presence of a CC-chemokine binding activity were subjected to successive rounds of screening and deconvolution until a single transfected HEK293 clone secreting a CC-chemokine binding activity was identified and called ChBP-59 (FIG. 1).

The cDNA encoding ChBP-59 (SEQ ID NO: 3) contains an Open Reading Frame (ORF; SEQ ID NO: 4) encoding a protein of 114 amino acids (SEQ ID NO: 5). The protein contains a potential secretion signal peptide sequence (residues 1-20), leading to a mature protein of 94 amino acids (SEQ ID NO: 6) that has no significant homology with known proteins.

Further features of ChBP-59 are three potential glycosylation sites (at Asparagine 39, 54, and 62, according to the numbering of the full protein), and a series of Cysteines that can be paired to form disulfide bridges (residues 32, 49, 53, 66, 85, 90, 95, and 104, according to the numbering of the full protein).

Example 2

Purification and Validation of ChBP-59 Expressed in HEK293 EBNA Cell Culture Supernatant and in TN5 Insect Cell Culture Supernatant as a His-tagged Recombinant Protein Materials and Methods a. Subcloning of ChBP-59 cDNA into the Expression Vectors pDEST8 and pEAK12d Using the Gateway™ Cloning Process The first stage of the Gateway cloning process involves a two step PCR reaction (PCR1 and PCR2) which generates the ORF of ChBP-59 flanked at the 5' end by an attB1 recombination site and Kozak sequence, and flanked at the 3' end by a sequence encoding an in frame 6 Histidine (6His) tag, a stop codon and the attB2 recombination site (Gateway compatible cDNA; FIG. 2). The PCR 1 reaction (in a final volume of 50 µl) contains: 1 µl (40 ng) of plasmid pEXP-Lib-ChBP-59, 1.5 µl dNTPs (10 mM), 10 µl of 10×Pfx polymerase buffer, 1 µl MgSO$_4$ (50 mM), 0.5 µl each of gene specific primer (100 µM) (59-attB1 forward and 59-attB2 reverse; SEQ ID NO: 7 and 8), and 0.5 µl Platinum Pfx DNA polymerase (Invitrogen). The PCR1 reaction was performed using an initial denaturing step of 95° C. for 2 minutes, followed by 12 cycles of 94° C. for 15 s; 55° C. for 30 s and 68° C. for 2 min; and a holding cycle of 4° C. The amplification products were directly purified using the Wizard PCR Preps DNA Purification System (Promega) and recovered in 50 µl sterile water according to the manufacturer's instructions.

The PCR2 reaction (in a final volume of 50 µl) contained 10 µl purified PCR1 product, 1.5 µl dNTPs (10 mM), 5 µl of 10×Pfx polymerase buffer, 1 µl MgSO$_4$ (50 mM), 0.5 µl of each Gateway conversion primer (100 µM) (GCP forward and GCP reverse; SEQ ID NO: 9 and 10) and 0.5 µl of Platinum Pfx DNA polymerase. The conditions for the PCR 2 reaction were: 95° C. for 1 minute; 4 cycles of 94° C. for 15 seconds, 50° C. for 30 seconds and 68° C. for 2 minutes; 25 cycles of 94° C. for 15 seconds, 55° C. for 30 seconds, and 68° C. for 2 minutes; holding cycle at 4° C. The resultant PCR products was visualized on 0.8% agarose gel in 1×TAE buffer (Invitrogen) and the band migrating at the predicted molecular mass (430 bp) was purified from the gel using the Wizard PCR Preps DNA Purification System (Promega) and recovered in 50 µl sterile water according to the manufacturer's instructions.

The second stage of the Gateway cloning process involves subcloning of the Gateway modified PCR product into the Gateway entry vector pDONR221. Five µl of purified product from PCR2 were incubated with 1.5 µl pDONR221 vector (0.1 µg/µl), 2 µl BP buffer and 1.5 µl of BP clonase enzyme mix (Invitrogen) in a final volume of 101 at room temperature for 1 hour. The reaction was stopped by addition of proteinase K 1 µl (2 µg/µl) and incubated at 37° C. for a further 10 minutes. An aliquot of this reaction (1 µl) was used to transform *E. coli* DH10B cells by electroporation as follows: a 25 µl aliquot of DH10B electrocompetent cells (Invitrogen) was thawed on ice and 1 µl of the BP reaction mix was added. The mixture was transferred to a chilled 0.1 cm electroporation cuvette and the cells electroporated using a BioRad Gene-Pulser™ according to the manufacturer's recommended protocol. SOC medium (0.5 ml), which had been pre-warmed to room temperature, was added immediately after electroporation. The mixture was transferred to a 15 ml snap-cap tube and incubated, with shaking (220 rpm) for 1 hour at 37° C. Aliquots of the transformation mixture (10 μl and 50 μl) were then plated on L-broth (LB) plates containing kanamycin (40 μg/ml) and incubated overnight at 37° C.

Plasmid mini-prep DNA was prepared from 5 ml cultures from 6 of the resultant colonies using a Qiaprep Turbo 9600 robotic system (Qiagen). Plasmid DNA (150-200 ng) was subjected to DNA sequencing with 21M13 and M13Rev primers using the BigDyeTerminator system (Applied Biosystems cat. no. 4336919) according to the manufacturer's instructions. Sequencing reactions were purified using Montage SEQ 96 cleanup plates (Millipore cat. no. LSKS09624) then analyzed on an Applied Biosystems 3700 sequencer.

Plasmid eluate (2 μl or approx. 150 ng) from one of the clones, which contained the correct sequence (pDONR221_ChBP-59-HIS) was then used in recombination reactions containing 1.5 μl of either pDEST8 vector or pEAK12d vector (0.1 μg/μl), 2 μl LR buffer and 1.5 μl of LR clonase (Invitrogen) in a final volume of 10 μl. The mixtures were incubated at room temperature for 1 hour. The reactions were stopped by addition of Proteinase K (2 μg) and incubated at 37° C. for a further 10 minutes. An aliquot of each reaction (1 μl) was used to transform *E. coli* DH10B cells by electroporation as follows: a 25 μl aliquot of DH10B electrocompetent cells (Invitrogen) was thawed on ice and 1 μl of the LR reaction mix was added. The mixture was transferred to a chilled 0.1 cm electroporation cuvette and the cells electroporated using a BioRad Gene-Pulser™ according to the manufacturer's recommended protocol. SOC media (0.5 ml), which had been pre-warmed to room temperature, was added immediately after electroporation. The mixture was transferred to a 15 ml snap-cap tube and incubated, with shaking (220 rpm) for 1 hour at 37° C. Aliquots of the transformation mixture (10 μl and 50 μl) were then plated on L-broth (LB) plates containing ampicillin (100 μg/ml) and incubated overnight at 37° C.

Plasmid mini-prep DNA was prepared from 5 ml cultures inoculated with six of the resultant colonies subcloned in each vector using a Qiaprep Bio Robot 8000 (Qiagen). Plasmid DNA (200-500 ng) in the pEAK12d vector was subjected to DNA sequencing with pEAK12F and pEAK12R primers (SEQ ID NO: 11 and 12). Similarly, plasmid DNA (200-500 ng) in the pDEST8 vector was subjected to DNA sequencing with pDEST8F and pDEST8R primers (SEQ ID NO: 13 and 14) as described above.

CsCl gradient purified maxi-prep DNA was prepared from a 500 ml culture of the sequence verified clones (pEAK12d_ChBP-59-HIS and pDEST8_ChBP-59-HIS,) using the method described by Sambrook J. et al., 1989 (in Molecular Cloning, a Laboratory Manual, $2^{nd}$ edition, Cold Spring Harbor Laboratory Press). Plasmid DNA was resuspended at a concentration of 1 μg/μl in sterile water (or 10 mM Tris-HCl pH 8.5) and stored at −20° C.

The primer sequences used in the different sub-/cloning steps are summarized in Table III.

b. Purification of Recombinant ChBP-59-HIS Expressed in HEK293 Cells

Cell culture supernatant (450 ml) from HEK293-EBNA cells was harvested 6 days post transfection with pEAK12d-ChBP-59-HIS and diluted with 2 volumes of 50 mM sodium phosphate buffer pH 7.5 containing 0.3 M NaCl and 10% (vol/vol) glycerol. The sample was filtered through a 0.22 μm filter membrane, then loaded at 1.7 ml/min at 4° C. onto a SX 16/10 column containing 5 ml $Ni^{2+}$-NTA agarose (Catalogue No: 30250; Qiagen) using an Äkta purifier system (Amersham Biosciences). Non-specifically bound material was removed by washing the column at 1.5 ml/min with 5 column volumes (CVs) of 50 mM sodium phosphate buffer pH 7.5 containing 0.3 M NaCl, 10% glycerol (Catalogue No: 49781; Fluka), followed by 50 CVs of the same buffer containing 1% Tween-20 (Catalogue No: 93773; Fluka) and finally with 30 CVs of the buffer without Tween-20. The column was eluted in 5 ml fractions with 10 CVs of 50 mM sodium phosphate buffer, pH 7.5, containing 0.3 M NaCl, 10% glycerol and 12.5 mM imidazole (Catalogue No: 56749; Fluka) at 2.5 ml/min followed by a gradient over 10 CVs to a maximum concentration of 250 mM imidazole, which was maintained for another 5 CVs.

ChBP-59-HIS-containing fractions were pooled and concentrated 10-fold using centrifugal filter devices with a cut-off of 10 kDa (Amicon Ultra-15, Catalogue No: UFC901096, Millipore). The concentrated pool was subjected to size exclusion chromatography as second step of purification. An SX200 10/300 GL column (bed volume of 25 ml; catalogue No: 17-5175-01; Amersham Biosciences), which has been first equilibrated in PBS (Phosphate Buffered Saline), was injected with 450 μl of the concentrated ChBP-59-HIS-containing protein eluate. The protein was eluted in fractions of 0.5 ml each at 2.5 ml/min. ChBP-59-HIS protein containing fractions were pooled, aliquoted, and stored at −80° C.

c. Purification of Recombinant ChBP-59-HIS Expressed in Insect Cells

*Trichoplusa ni* insect cells of the commercial strain High-Five (Catalogue No: 10486; Invitrogen) were cultured in Excell405 medium (Catalogue No: 24405; JRH Biosciences). The cells were infected with recombinant baculovirus generated from the expression plasmid pDEST8-ChBP-59-HIS. The culture supernatant was harvested and clarified by centrifugation for 30 minutes at 500 g. A total of 1200 ml supernatant was harvested from the cells, and diluted in 7 volumes of ice-cold 50 mM $NaPO_4$ buffer, pH 7.5, containing 0.3 M NaCl and 10% glycerol, and subsequently filtered through a 0.22 μm filter. The filtered, diluted sample was passed over 15 ml $Ni^{2+}$NTA agarose resin (Catalogue No: 30250; Qiagen), loaded in a SX 26/10 column at 7 ml/min and 4° C. The column was washed at 2.5 ml/min with 5 CVs of 50 mM sodium phosphate buffer, pH 7.5, containing 0.3 M NaCl, 10% glycerol, followed by 50 CVs of the same buffer containing 1% Tween20 (Catalogue No: 93772; Fluka) and finally with 30 CVs of the buffer without Tween20 to remove all traces of detergent. Nonspecifically-bound material was removed by washing the column at 2.5 ml/ml with 10 CV of 50 mM Sodium phosphate buffer, pH 7.5, containing 0.3 M NaCl, 10% glycerol and 12.5 mM imidazole at 2.5 ml/min. The column was then eluted at 2.5 ml/min with a linear imidazole gradient from 12.5 mM to 250 mM over 10 CVs. The column was eluted for another 5 CV at 250 mM imidazole. Selected fractions were analyzed by SDS-PAGE and Western blotting using anti-Histidine tag antibodies.

ChBP-59-HIS-containing fractions were pooled and subjected to a second purification step based on anion exchange chromatography. The pooled fractions of the post-$Ni^{2+}$ affinity chromatography were diluted 10-fold in 25 mM Tris-HCl buffer (pH 8) containing 0.03 M NaCl, and loaded onto a SX16/10 column containing 15 ml of Q sepharose at 5 ml/min at 4° C. Then, the column was washed with 10 CVs of buffer and subsequently eluted by applying a salt gradient from 0.03 M to 1 M NaCl-containing buffer over 10 CVs. Seven ml fractions were collected and analyzed by SDS-PAGE. ChBP-59-HIS containing fractions were pooled and the pool was divided in half, and either dialyzed against 100 volumes of 25 mM Tris-HCl buffer, pH 8, or against PBS. The protein concentration of the pool was determined by UV spectrophotometry at 280 nm, and the pooled protein fractions were aliquoted and stored at −80° C.

d. Western Blot and Crosslinking Analysis of Recombinant ChBP-59-HIS

The column eluates were diluted 1:1 with 2× sample buffer (Invitrogen) containing 100 mM DTT and boiled for 5 minutes. The samples and a HIS-tagged molecular weight standard (Catalogue No: LC5606; Invitrogen) were electrophoresed on a 10% Bis-Tris gel run in MES-buffer at 200 V for 35 min. The electrophoresed proteins were electro-transferred onto a 0.45 μm nitrocellulose membrane (Catalogue No: LC2001; Invitrogen) in transfer buffer (39 mM glycine, 48 mM Tris base, and 20% methanol, pH 8.3) for 50 minutes at room temperature, using a constant current of 290 mA. The membrane was blocked by incubating in 20 ml blocking solution (0.1% Tween 20, 5% milk powder in PBS), for 1 hour at room temperature on a rocker platform. The membrane was then incubated in 15 ml of the solution containing the primary anti-Histidine tag antibody (diluted 1:1000 in 0.1% Tween 20, 2.5% milk powder in PBS) for 2 hours at room temperature with shaking. The primary antibodies used were His-probe H-15 (sc-803; Santa Cruz Biotechnology) or His-probe G-18 (sc-804; Santa Cruz Biotechnology). The membrane was rinsed in wash buffer (0.1% Tween 20 in PBS) and washed with 3 changes of wash buffer (10 minutes each). The membrane was then incubated in HRP-conjugated secondary antibody (diluted 1:3000 in 0.1% Tween 20, 2.5% milk powder in PBS) for 2 hours at room temperature with shaking. The membrane was washed again as described previously. Finally, the membrane was blotted dry, and antibody staining was visualized using the ECL™ Western Blotting Detection Reagents kit (Catalogue No: RPN2106; Amersham Pharmacia), according to manufacturer's instructions.

Results

The ORF encoding for ChBP-59 was transferred in plasmids allowing high production levels in either mammalian or insect cells using a commercial kit (Gateway™) as a recombinant, histidine-tagged protein (ChBP-59-HIS; FIG. 2).

The plasmid containing the ORF of clone 59 (pEXP-Lib_ChBP-59) was used as PCR template to generate a Gateway cloning system compatible 6 Histidine-tagged version of ChBP-59 cDNA (SEQ ID NO: 15). The ORF for ChBP-59-HIS (SEQ ID NO: 16) encodes for a 120 amino acids sequence (SEQ ID NO: 17) which can be then matured by elimination of the signal sequence as 100 amino acid sequence (SEQ ID NO: 18). The Gateway entry vector pDONR221_ChBP-59-HIS, and the expression constructs pDEST8_ChBP-59-HIS, and pEAK12d_ChBP-59-HIS were generated (FIG. 3).

Figure 4:
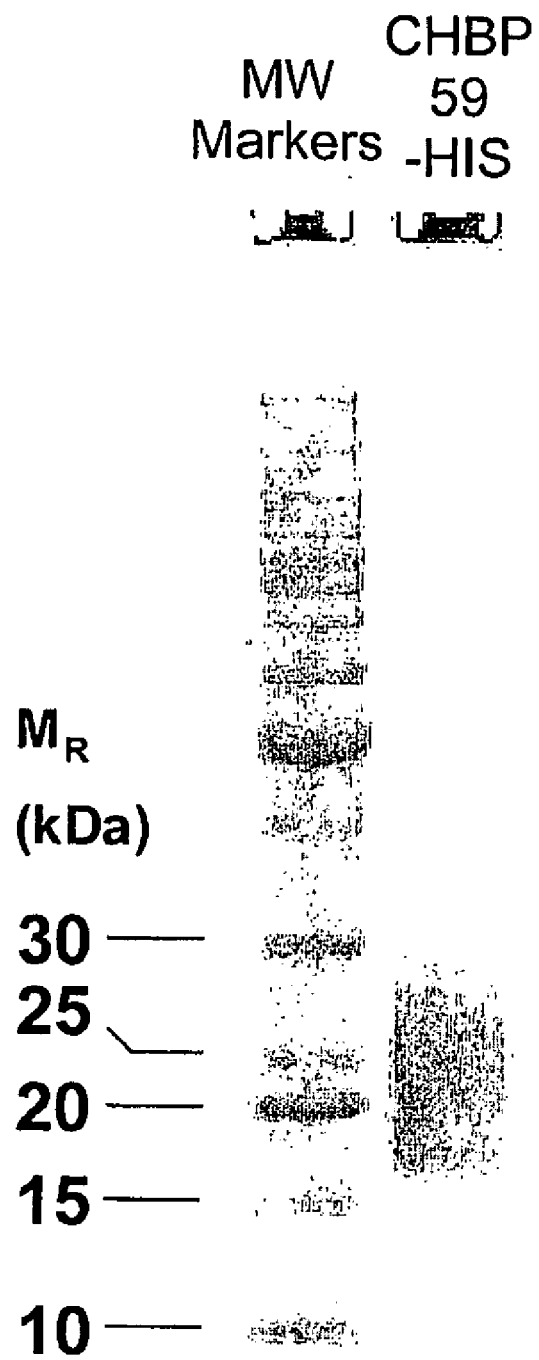
FIG. 4: 10% SDS-polyacrylamide gel (SDS-PAGE) stained with Coomassie blue solution showing the molecular weight of ChBP-59-HIS purified from HEK293 and baculovirus-infected TN5 (labeled BV in FIG. 4) cells using $Ni^{2+}$ affinity and anion exchange chromatography. The molecular weight standards are indicated on the left ($M_R$).

Recombinant ChBP-59-HIS was purified from either pEAK12d-ChBP-59-transfected HEK293 EBNA cell supernatant (using Ni2+-affinity chromatography followed by size exclusion chromatography) or pDEST8-ChBP-59-HIS-infected TN5 insect cells (using Ni2+-affinity chromatography followed by anion exchange chromatography). The Coomassie blue staining of a SDS-PAGE in which the purified protein has been loaded suggests that ChBP-59-HIS was expressed and purified as a mixture of differently post-translationally modified forms, possibly by glycosylated as shown for another tick protein expressed in insect cells (Alarcon-Chaidez FJ et al., 2003). In fact, the protein appears as a smeared band, with an average molecular weight of around 20-25 Kd for the recombinant protein expressed in HEK293 and TN5 cells (FIG. 4).

The presence of recombinant ChBP-59-HIS during the different purification steps from both HEK293 and insect cell supernatants was followed by Western blot with anti-Histidine tag as primary antibodies. The N-terminal of the purified, mature sequence has been sequenced, confirming that the sequence EDDEDYGDLG forms the N-terminus of the mature protein.

The CC-chemokine binding activity of ChBP-59-HIS final preparations were compared with the activity observed using the positive control (the viral CC-chemokine binding protein vCCI) or the saliva from *Rhipicephalus sanguineus*, using the crosslinking assay used initially to characterize the activity in tick saliva.

Figure 5:
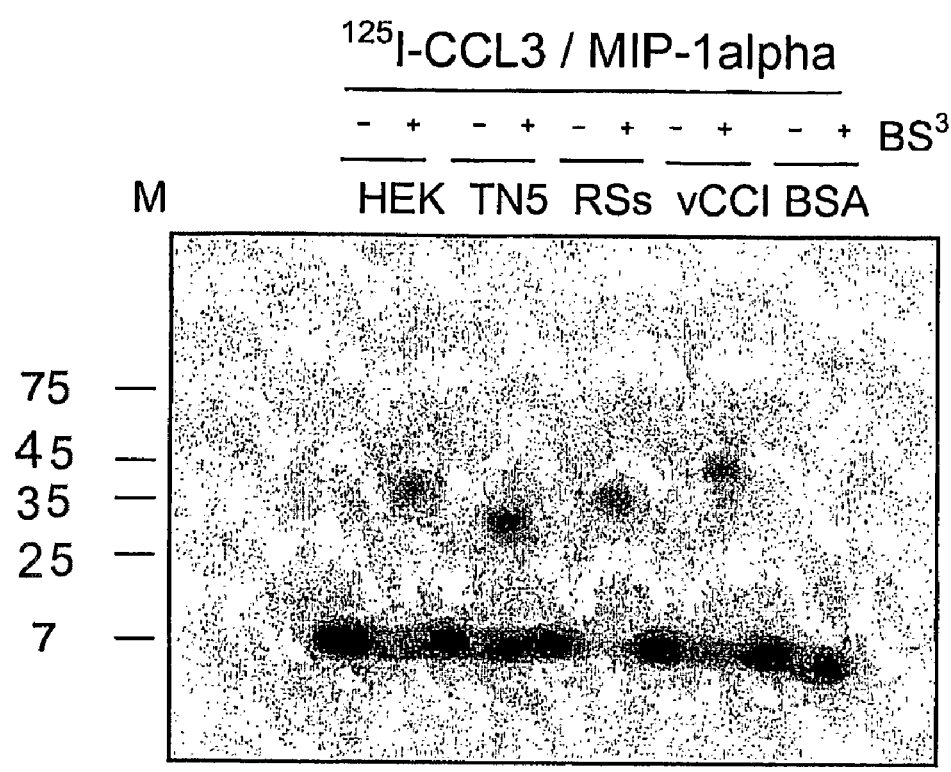
FIG. 5: Autoradiography of the SDS-PAGE showing the complexes formed by crosslinking $^{125}$I-labeled CC-chemokine CCL3/MIP-1 alpha with recombinant ChBP-59-HIS expressed in HEK293 (HEK) or TN5 insect cells (TN5) protein, with the viral CC-chemokine binding protein (vCCI, positive control), with crude tick saliva from *Rhipicephalus sanguineus* (RSs), or with Bovine Serum Albumin (BSA, negative control). The unlabeled proteins were added to the radiolabeled CC-chemokine ($^{125}$I-CCL3/MIP-1alpha) in presence (+) or absence (−) of the cross-linking agent ($BS^3$). The molecular weight standards (in Kd) are indicated on the left (M).

In SDS-PAGE, the free $^{125}$I-labeled CC-chemokine CCL3/MIP-1alpha migrates as an 8 kDa band. When the crosslinking agent is added, a part of the radioactivity is retained in a protein complex having a molecular weight of 28-40 kDa, as it can be determined approximately on the basis of the shifted band, in both samples containing recombinant ChBP-59 and in tick saliva (FIG. 5). The molecular weight of the shifted band is slightly different amongst these three samples probably due to the different kinds and level of post-translational modification of the protein (glycosylation, in particular) in each type of host cell.

Given that the molecular weight for mature ChBP-59-HIS polypeptide (100 amino acids) is around 11 Kd, this recombinant protein appears to be active when expressed in Eukaryotic host cells wherein it is post-translationally modified isoforms. These modifications may account for up to 10-20 Kd (as suggested also by the Coomassie staining in FIG. 4) and are probably due mostly to alternative glycosylation.

This experiment, which has been confirmed using other radiolabeled CC-chemokines (CCL5/RANTES and CCL2/MCP-1), demonstrates the activity of ChBP-59 (as natural protein and as a recombinant, histidine-tagged protein) as a CC-chemokine binding protein.

Example 3

Characterization of Recombinant ChBP-59 Inhibitory Activity on CC-Chemokines

Materials and Methods

SPA Assays

The SPA assay was designed for detecting molecules interfering with the chemokine/chemokine receptor interaction as described in the literature (Alouani S, 2000) and above (Example 1).

b. CC-Chemokine Induced Chemotaxis

Chemotaxis experiments were performed on L1.2 cells (mouse pre B-cell line) stably expressing human chemokine receptor 5 (CCR5). L1.2/CCR5 cells were maintained in RPMI 1640 culture medium (Invitrogen, catalogue no: 31870-025) supplemented with 10% FCS (Fetal calf Serum; TerraCell, catalogue no: CS-C08-1000-A), 2 mM L-glutamine (Invitrogen catalogue no: 25030-024), 1 mM sodium pyruvate (Sigma, catalogue no: S8636), and 1% penicillin-streptomycin (Invitrogen catalogue no: 15140-148).

Twenty four hours before performing the chemotaxis assay, cells were treated with 5 mM butyric acid (Sigma catalogue no: B-5887). The next day, cells were harvested by centrifugation for 15 minutes at 230×g, and resuspended at a cell density of 1×10⁶ cells/ml in RPMI 1640 medium without phenol red indicator (Invitrogen catalogue no: 32404-014), supplemented with 10% FCS. CCL3/MIP-1alpha was suspended at 0.01 mg/ml in the same medium and eleven serial, 4-fold dilutions were prepared. Similarly, recombinant ChBP-59-HIS, purified from TN5 cells was serially diluted 5-fold starting from 316 ng/ml and mixed in equal amounts with medium containing 2 nM CCL3/MIP-1alpha. Aliquots (32 ml) of the serially diluted chemokine solution or chemokine-ChBP-59-HIS solution were added in triplicate to the lower compartments of a chemotaxis chamber and an 8-µm pore size filter unit (Neuroprobe ChemoTx System, catalogue no: 101-8) was carefully placed on top of the lower compartment. The L1.2/CCR5 cell suspension (20 µl) was added to the top compartment and the chemotaxis chamber and incubated for 2 hours at 37° C. in a humidified, 5% CO2 incubator.

The lid of the chemotaxis chamber was then removed and discarded. A 96-well funnel plate (Neuroprobe ChemoTx System catalogue No: FP1) was placed upside down on top of the lower compartment of the chemotaxis chamber. A black-matrix plate (Vitaris catalogue no: 3915) was then placed upside down on top of the funnel plate and the chemotaxis chamber/funnel plate/black-matrix plate assembly was flipped over. The medium in the lower compartment of the chemotaxis chamber was then transferred into the black-matrix plate by centrifugation for 2 minutes at 700×g. The black-matrix plate containing the migrated cells was sealed and frozen for 2 hours at −80 ° C. The number of cells that had migrated into the lower compartment of the chemotaxis chamber was determined indirectly using the CyQUANT cell proliferation assay kit (Molecular Probes catalogue no: C7026). The black plate was thawed and cells were thoroughly resuspended in 200 ml of cell lysis buffer containing the dye provided in the kit, according to manufacturer's instructions. Fluorescence was measured in a Wallac Victor plate reader using 480 nm/520 nm excitation/emission wavelengths.

Results

The CC-chemokine binding properties of ChBP-59-HIS were studied in a SPA (Scintillation Proximity Assay) and in a CC-chemokine induced cell migration assay.

Figure 6:
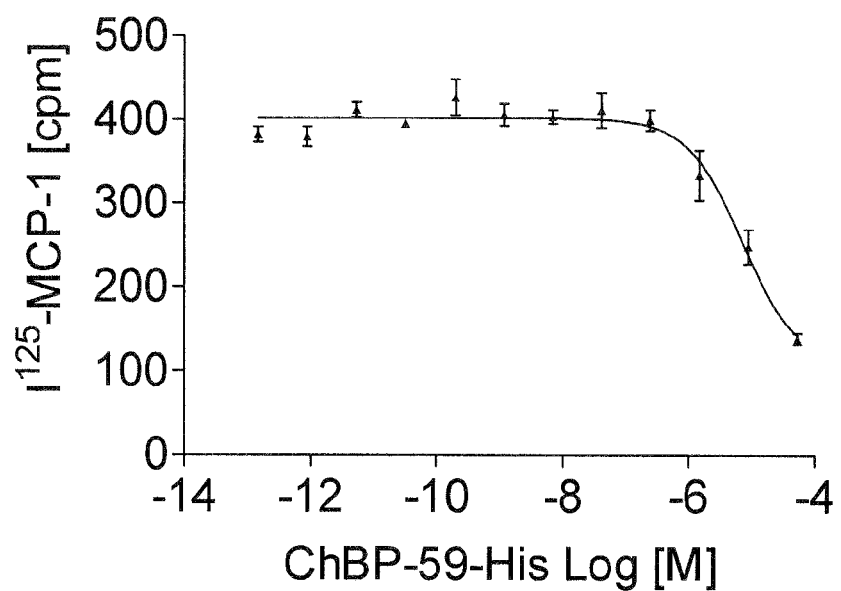
FIG. 6: CC-chemokine binding activity of recombinant ChBP-59-HIS purified from baculovirus-infected insect cells. The inhibitory effect of ChBP-59-HIS was measured by addition of serial dilutions of the recombinant protein to a constant amount of a SPA bead-immobilized chemokine receptor (CCR5) and of radiolabeled CCL5/RANTES (A), CCL3/MIP-1 alpha (B), or CCL2/MCP-1 (C).

SPA shows that serial dilution of recombinant ChBP-59-HIS challenging specific chemokine/chemokine receptor pairs can inhibit this interaction. In fact the SPA signal due to the interaction of the bead with the radiolabeled chemokine by means of the chemokine receptor decrease significantly at low ChBP-59-HIS molar concentrations (FIG. 6). The ChBP-59-HIS affinity, as determined with this approach, seems higher for CCL3/MIP-1α ($EC_{50}$ for the inhibition was 12 pM) than for CCL2/MCP-1 and CCL5/RANTES ($EC_{50}$ for the inhibition was in the micromolar range for both these CC-chemokines). This suggests a possible binding preference of ChBP-59 for some CC-chemokines.

Figure 7:
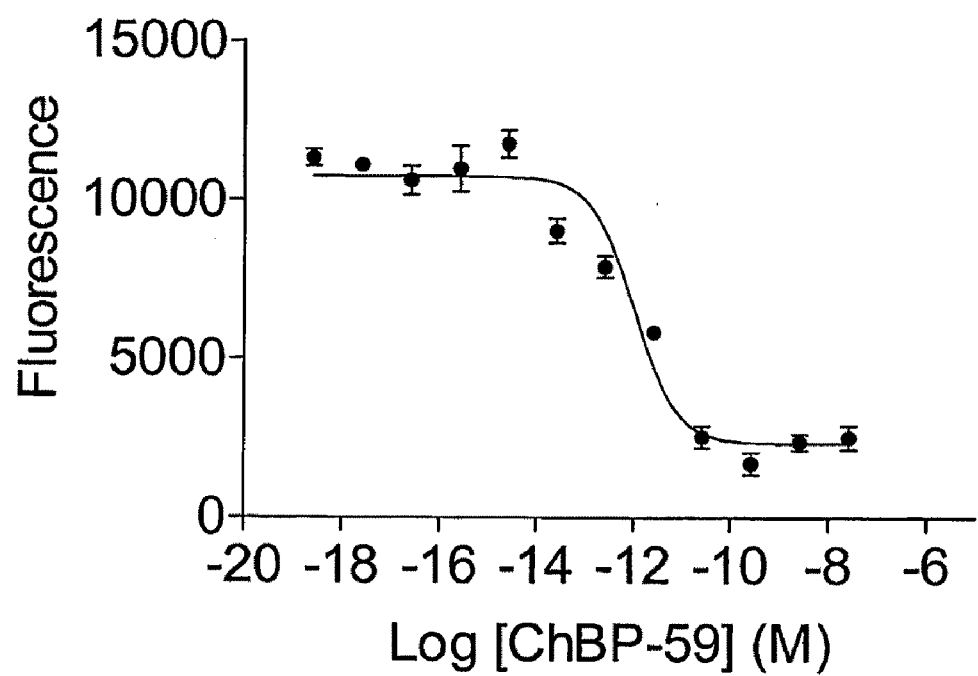
FIG. 7: Inhibitory effect of ChBP-59-HIS in an assay measuring CCL3/MIP-1alpha-induced and CCL5/RANTES-induced chemotaxis on mouse L1.2 cells expressing the CC-chemokine receptor CCR5. The CC-chemokine was added at a constant concentration (1.0 nM) in the different samples having increasing molar concentration (expressed in Log) of ChBP-59-HIS. The Fluorescence units are proportional to the number of migrated cells.

Finally, ChBP-59-HIS can efficiently inhibit CC-chemokine-induced chemotaxis, in particular CCL3/MIP-1α-induced and CCL5/RANTES-induced chemotaxis of L1.2-CCR5. Again, the number of migrated cells following the exposure to a CC-chemokine was decreased proportionally with the concentration of ChBP-59-HIS added in the assay, and consequently inhibiting the interaction of the cells with the CC-chemokine. This effect is particularly important since it can be achieved at low ChBP-59-HIS molar concentrations (below $10^{-10}$ M; FIG. 7).

Example 4

Characterization of ChBP-59 Activity In vivo

Materials and Methods a) Animals

Male Balb/C or C57B6 mice (18-22 g) were used throughout these experiments. Animals were housed in a temperature-controlled room with free access to water and food.

b) Peritoneal Cell Recruitment

Figure 9:
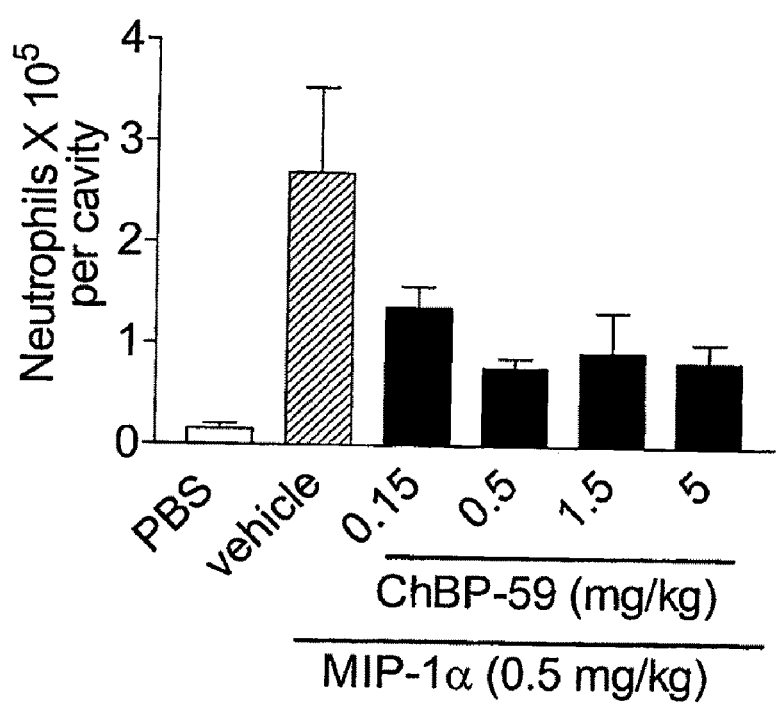
FIG. 9: Dose response of the inhibitory effect of ChBP-6His on CCL3/MIP-1α induced peritoneal recruitment in two murine strains. ChBP-59-6His was administered s.c. at various doses 45 min before the administration of CCL3/MIP-1α at 0.5 mg/kg i.p. After 18 h the number of granulocytes recruited into the peritoneal cavity were enumerated. A) Balb/C B) C57B6 mouse strain.

Eight- to 12-week-old male Balb/c or C57B6 mice were injected intraperitoneally with 200 µl of phosphate buffer saline (PBS, pH 7.4) or human MIP-1α (0.5 mg/Kg) diluted into 200 µl PBS. To test inhibition, doses ranging from 0.15 to 5 mg/kg of ChBP-59 in 200 µl PBS were administered s.c. 45 min before human MIP-1α administration (0.5 mg/kg i.p.). At 18 h postinjection mice were sacrificed, the peritoneal cavity was washed two times with 3 mL of ice-cold PBS, and the total lavage was pooled for individual mice. Total cell counts were performed in a modified Neubauer chamber using Turk's stain. Differential cell counts were performed on cytospin preparations (Shandon III) stained with May Grunwald-Giemsa using standard morphologic criteria to identify cell types. The results are presented as the number of cells per cavity (FIG. 8 and FIG. 9).

c) Intravital Microscopy

For each experiment, 0.15 mg/Kg of human MIP-1α in 0.1 mL of PBS was administered locally by s.c. injection beneath the right scrotal skin using a 30G needle, 1 h before exteriorization. To test inhibition, the solution of ChBP-59 (0.5 mg/kg) plus MIP-1α (0.15 mg/Kg) in 100 µl PBS was prepared 15 min before intrascrotal injection administration. The left cremaster was then prepared for intravital microscopy. Briefly, an incision was made in the scrotal skin to expose the left cremaster muscle, which was then carefully removed from the associated fascia. A lengthwise incision was made on the ventral surface of the cremaster muscle using a cautery. The testicle and the epididymis were separated from the underlying muscle and were moved into the abdominal cavity. The muscle was then spread out over an optically clear-viewing pedestal and was secured along the edges with 4-0 suture. The exposed tissue was superfused with warm bicarbonate-buffered saline (pH 7.4). An intravital microscope (Olympus BX50F4; Japan) with a 20× objective lens and a 10× eyepiece was used to examine the cremasteric microcirculation. A video camera (5100 HS; Panasonic, Osaka, Japan) was used to project the images onto a monitor, and the images were recorded for playback analysis using a conventional videocassette recorder.

Figure 10:
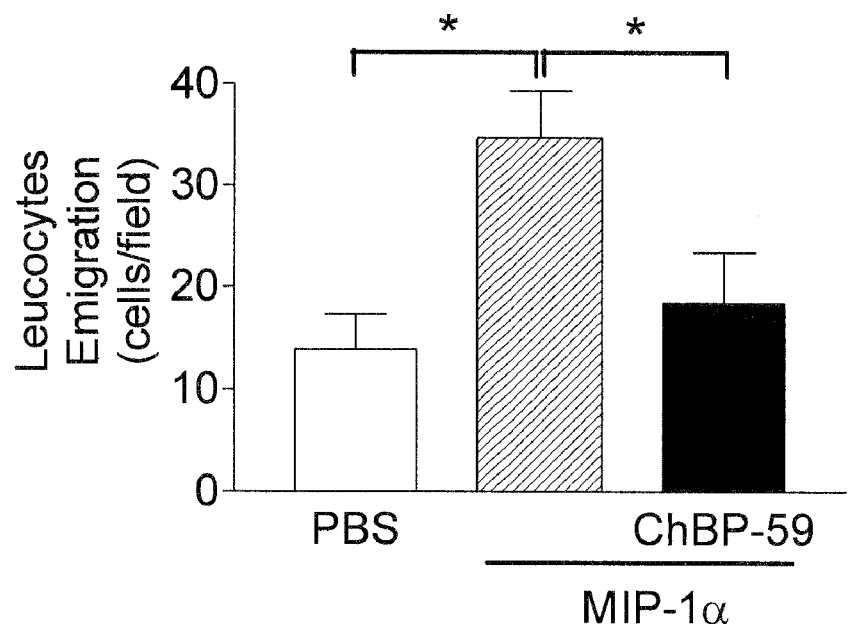
FIG. 10: Visualization of the cellular recruitment process by intravital microscopy. MIP-1α (0.15 mg/kg) or ChBP-59 (0.5 mg/kg) and MIP-1α (0.15 mg/kg) together were injected intrascrotally. After 1 h, the cremaster muscle was removed and the circulation was observed with the intravital microscope and recordings were made for off-line analysis. A) Rolling. B) Adhesion. C) Emigration.

Single, unbranched cremasteric venules (25-40 µm in diameter) were selected, and to minimize variability, the same section of cremasteric venule was observed throughout the experiment. The number of rolling, adherent, and emigrated leukocytes was determined offline during video playback analysis. Rolling leukocytes were defined as those cells moving at a velocity less than that of erythrocytes within a given vessel. The flux of rolling cells was measured as the number of rolling cells passing by a given point in the venule per minute. A leukocyte was considered to be adherent if it remained stationary for at least 30 s, and total leukocyte adhesion was quantified as the number of adherent cells within a 100-µm length of venule. Leukocyte emigration was defined as the number of cells in the extravascular space within area of 50 µm of distance from the venule. Only cells adjacent to and clearly outside the vessel under study were counted as emigrated. At the end of each experiment whole blood was drawn by cardiac puncture. Total cell counts were performed in a modified Neubauer chamber using Turk's stain. Results are presented in FIG. 10.

d) Sensitization and Induction of Th2 Cellular Recruitment into the Lungs

Figure 11:
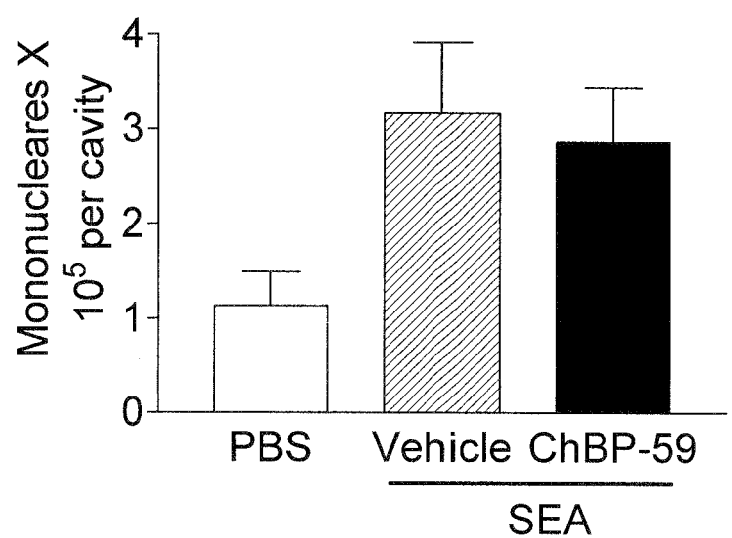
FIG. 11: Inhibitory effect of ChBP-59-6His on Th2 cellular recruitment into the lungs. Mice were sensitized with 2,500 *Schistosoma mansoni* eggs i.p. on day 1 and day 7. Seven days later they were challenged with *Schistosoma* egg antigen (SEA) intranasally. Six days later ChBP-6His was administered s.c. at 0.5 mg/kg 45 min prior to a second SEA challenge intratracheally, and a second administration of ChBP-6His at 0.5 mg/kg was given 24 h later. After 48 h BAL fluid was removed for cellular enumeration. A) total cells. B) eosinophils. C) mononuclear cells.

Mice were immunized intraperitoneally with 2500 isolated S. mansoni eggs at days 0 and 7 of the protocol. On day 14 mice were given an intranasal challenge of 10 µg in 10 µL of PBS to localize the response to the airway. Mice were then rechallenged 6 days later by intratracheal administration of 10 µg in 25 µL of PBS or with PBS alone (vehicle). To test inhibition, ChBP-59 (0.5 mg/kg) was administered s.c. 45 min before and 24 h after antigen challenge. At 48 h postinjection mice were sacrificed and lungs were filled in situ with 0.3 mL of sterile PBS via a tracheal cannula. Fluid was withdrawn from the lungs after gentle massage to remove cells and collected in a plastic tube on ice. This procedure was repeated three times, and the cell suspensions recovered from each animal were pooled for individual mice. Total cell counts were performed in a modified Neubauer chamber using Turk's stain. Differential cell counts were performed on cytospin preparations (Shandon III) stained with May Grunwald-Giemsa using standard morphologic criteria to identify cell types. The results are presented as the number of cells per lungs (see FIG. 11).

e) OVA-induced Airway Inflammation

Figure 12:
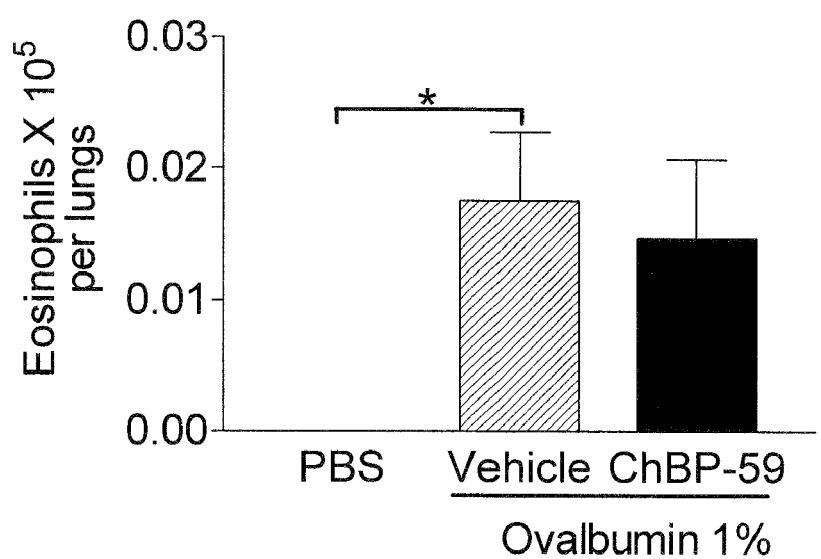
FIG. 12: Inhibitory effect of ChBP-59-6His on ovalbumin induced lung inflammation. Mice were immunized twice with ovalbumin in $Al(OH)_3$ (alum). After 14 d, they were challenged with a 1% ovalbumin aerosol challenge for 20 min. ChBP-59-6His at 0.5 mg/kg was administered s.c. 45 min prior to the aerosol challenge and subsequently every 12 h. BAL was taken 2 days after the aerosol challenge for cellular enumeration. A) total cells. B) eosinophils. C) mononuclear cells.

To induce airway responses to OVA, mice were sensitized by an s.c. injection of 10 µg of OVA precipitated in 2 mg of aluminum hydroxide (2%) in a total volume of 200 µl. Fourteen days after sensitization, mice were aerosolized with PBS or a solution of OVA 1% diluted in PBS during 20 min. To test inhibition, CbBP-59 (0.5 mg/kg) was administered s.c. 45 min before and every 12 h after antigen challenge. At 48 h postinjection mice were sacrificed and lungs were filled in situ with 0.3 mL of sterile PBS via a tracheal cannula. Fluid was withdrawn from the lungs after gentle massage to remove cells and collected in a plastic tube on ice. This procedure was repeated three times, and the cell suspensions recovered from each animal were pooled for individual mice. Total cell counts were performed in a modified Neubauer chamber using Turk's stain. Differential cell counts were performed on cytospin preparations (Shandon III) stained with May Grunwald-Giemsa using standard morphologic criteria to identify cell types. The results are presented as the number of cells per lungs (see FIG. 12).

f) Bleomycin-Induced Lung Injury

Figure 13:
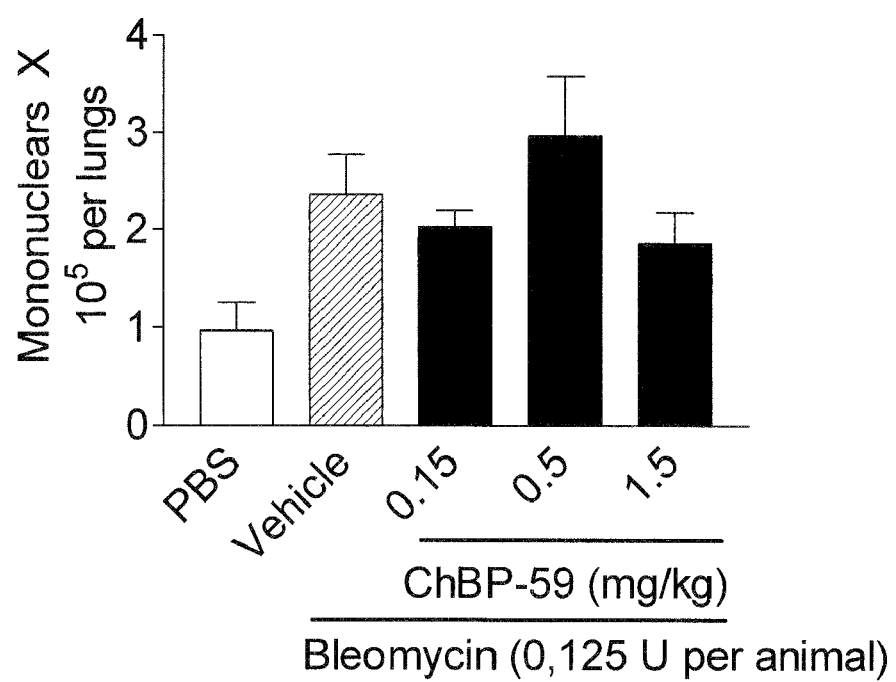
FIG. 13: Inhibitory effect of ChBP-59-6His on bleomycin induced lung inflammation. Mice were sensitised with 0.125 units of bleomycin intratracheally on day 0. Prior to the sensitization they were treated with ChBP-59-6His at 0.5 mg/kg s.c. 45 min before the bleomycin administration, and subsequently with the same dose every 12 h for the following 12 days. The mice that were analysed on day 2 after sensitization were treated with 3 doses of ChBP-59-6H is. At day 2 or day 8 the BAL was taken for cellular enumeration. A) total cells. B) eosinophils. C) mononuclear cells.
Figure 13:
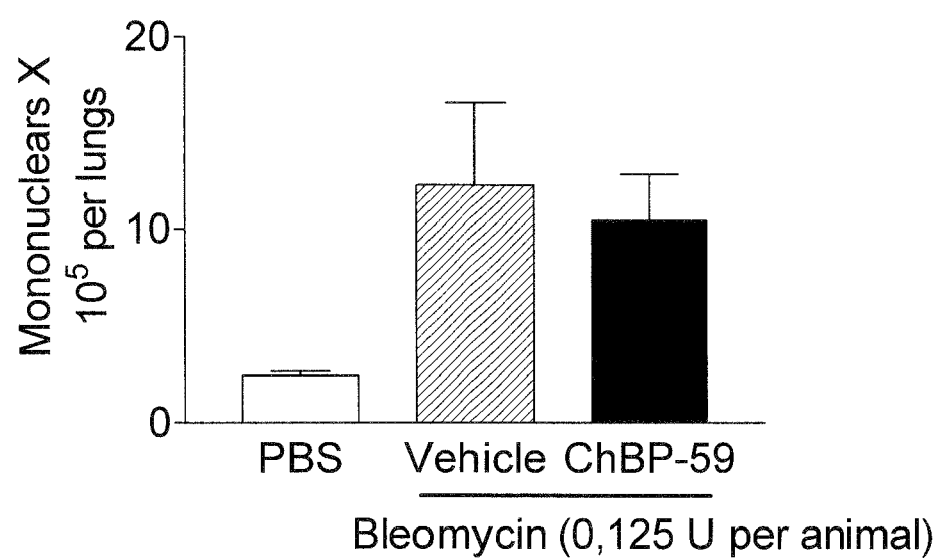

Under anesthesia (ketamine 3.2 mg/mouse and xylazine 0.16 mg/mouse), 0.125 U Bleomycin (Bonar, Laboratório Sintética, Brasil) in 30 µl PBS was instilled into the mouse trachea with a 25-G needle inserted between the cartilaginous rings of the trachea. Control animals received saline alone. The tracheostomy site was sutured, and the animals were allowed to recover. To test inhibition, ChBP-59 (0.5 mg/kg) was administered s.c. 45 min before and every 12 h after bleomycin insillation. At 2 or 8 days postinsillation mice were sacrificed and lungs were filled in situ with 0.3 mL of sterile PBS via a tracheal cannula. Fluid was withdrawn from the lungs after gentle massage to remove cells and collected in a plastic tube on ice. This procedure was repeated three times, and the cell suspensions recovered from each animal were pooled for individual mice. Total cell counts were performed in a modified Neubauer chamber using Turk's stain. Differential cell counts were performed on cytospin preparations (Shandon III) stained with May Grunwald-Giemsa using standard morphologic criteria to identify cell types. The results are presented as the number of cells per lungs (see FIG. 13).

g) Statistical Analysis

All results are presented as the means±SEM. Normalized data were analyzed by one-way ANOVA, and differences between groups were assessed using Student-Newman-Keuls post-test. A p value <0.05 was considered to be significant.

Results

ChBP-59 was tested for its ability to inhibit the recruitment of cells induced by MIP-1α into the peritoneal cavity. At a single dose of 1.5 mg/kg, the most significant inhibition was observed for granulocytes, which is not the case in the human system where MIP-1α recruits predominantly monocytes. A second experiment was performed with doses ranging from 0.15-5 mg/kg on two murine strains, Balb/C and C57B6. The number of eosinophils recruited in the Balb/C mice was insufficient to quantitate their inhibition, but good inhibition of neutrophils was observed in both strains at all doses, and 0.5 mg/kg was selected for the subsequent experiments. Intravital microscopy confirmed that ChBP-59 inhibited all three steps involved in the recruitment process, rolling, adhesion and emigration.

Due to potent inhibition of eosinophil recruitment, ChBP-59 was tested in its ability to inhibit the recruitment of these cells into the lung in a Th2 sensitisation model, as well as in ovalbumin induced lung inflammation. In both cases potent inhibition of eosinophil recruitment was observed, with little effect on mononuclear cells. Since bleomycin induced lung inflammation is mediated by the granulocyte neutrophil, it was also tested in this model, and significant inhibition of neutrophils was observed at both 2 days and 8 days after sensitization.

These results allow the interpretation that it would be likely to inhibit mononuclear recruitment in the human.

Therefore, it can be concluded that ChBP-59 is a novel protein having CC-chemokine binding properties, thereby inhibiting the action of chemokines. This protein can be usefully applied in human medicine as an anti-inflammatory compound, as well as in problems of medical and veterinary indications related to the parasitic effects of ticks, including tick-borne infectious agents. Molecules based on the proteins of the invention and interfering with the function of such proteins, might disrupt the tick life-cycle, control ectoparasites and their pathogens, or reduce tick's ability to transmit disease-causing organisms.

TABLE I

| Amino Acid | Synonymous Group | More Preferred Synonymous Groups |
|---|---|---|
| Ser | Gly, Ala, Ser, Thr, Pro | Thr, Ser |
| Arg | Asn, Lys, Gln, Arg, His | Arg, Lys, His |
| Leu | Phe, Ile, Val, Leu, Met | Ile, Val, Leu, Met |
| Pro | Gly, Ala, Ser, Thr, Pro | Pro |
| Thr | Gly, Ala, Ser, Thr, Pro | Thr, Ser |
| Ala | Gly, Thr, Pro, Ala, Ser | Gly, Ala |

TABLE I-continued

| Amino Acid | Synonymous Group | More Preferred Synonymous Groups |
|---|---|---|
| Val | Met, Phe, Ile, Leu, Val | Met, Ile, Val, Leu |
| Gly | Ala, Thr, Pro, Ser, Gly | Gly, Ala |
| Ile | Phe, Ile, Val, Leu, Met | Ile, Val, Leu, Met |
| Phe | Trp, Phe, Tyr | Tyr, Phe |
| Tyr | Trp, Phe, Tyr | Phe, Tyr |
| Cys | Ser, Thr, Cys | Cys |
| His | Asn, Lys, Gln, Arg, His | Arg, Lys, His |
| Gln | Glu, Asn, Asp, Gln | Asn, Gln |
| Asn | Glu, Asn, Asp, Gln | Asn, Gln |
| Lys | Asn, Lys, Gln, Arg, His | Arg, Lys, His |
| Asp | Glu, Asn, Asp, Gln | Asp, Glu |
| Glu | Glu, Asn, Asp, Gln | Asp, Glu |
| Met | Phe, Ile, Val, Leu, Met | Ile, Val, Leu, Met |
| Trp | Trp, Phe, Tyr | Trp |

TABLE II

| Amino Acid | Synonymous Group |
|---|---|
| Ser | D-Ser, Thr, D-Thr, allo-Thr, Met, D-Met, Met(O), D-Met(O), L-Cys, D-Cys |
| Arg | D-Arg, Lys, D-Lys, homo-Arg, D-homo-Arg, Met, Ile, D-.Met, D-Ile, Orn, D-Orn |
| Leu | D-Leu, Val, D-Val, AdaA, AdaG, Leu, D-Leu, Met, D-Met |
| Pro | D-Pro, L-1-thioazolidine-4-carboxylic acid, D-or L-1-oxazolidine-4-carboxylic acid |
| Thr | D-Thr, Ser, D-Ser, allo-Thr, Met, D-Met, Met(O), D-Met(O), Val, D-Val |
| Ala | D-Ala, Gly, Aib, B-Ala, Acp, L-Cys, D-Cys |
| Val | D-Val, Leu, D-Leu, Ile, D-Ile, Met, D-Met, AdaA, AdaG |
| Gly | Ala, D-Ala, Pro, D-Pro, Aib, .beta.-Ala, Acp |
| Ile | D-Ile, Val, D-Val, AdaA, AdaG, Leu, D-Leu, Met, D-Met |
| Phe | D-Phe, Tyr, D-Thr, L-Dopa, His, D-His, Trp, D-Trp, Trans-3,4, or 5-phenylproline, AdaA, AdaG, cis-3,4, or 5-phenylproline, Bpa, D-Bpa |
| Tyr | D-Tyr, Phe, D-Phe, L-Dopa, His, D-His |
| Cys | D-Cys, S--Me--Cys, Met, D-Met, Thr, D-Thr |
| Gln | D-Gln, Asn, D-Asn, Glu, D-Glu, Asp, D-Asp |
| Asn | D-Asn, Asp, D-Asp, Glu, D-Glu, Gln, D-Gln |

TABLE II-continued

| Amino Acid | Synonymous Group |
|---|---|
| Lys | D-Lys, Arg, D-Arg, homo-Arg, D-homo-Arg, Met, D-Met, Ile, D-Ile, Orn, D-Orn |
| Asp | D-Asp, D-Asn, Asn, Glu, D-Glu, Gln, D-Gln |
| Glu | D-Glu, D-Asp, Asp, Asn, D-Asn, Gln, D-Gln |
| Met | D-Met, S--Me--Cys, Ile, D-Ile, Leu, D-Leu, Val, D-Val |

TABLE III

| Primer | Sequence (5'-3') |
|---|---|
| 59-attB1 forward | AAGCAGGCTTCGCCACCATGACGTTTAAGGCTTGCATTG |
| 59-attB2 reverse | *GTGATGGTGATGGTGATTCTTCTTGTCTCGCCAATTG* |
| GCP forward | GGGGACAAGTTTGTACAAAAAAGCAGGCTTC<u>GCCACC</u> |
| GCP reverse | GGGGACCACTTTGTACAAGAAAGCTGGGTTTCAA*TGGTG ATGGTGATGGTG* |
| pEAK12F | GCCAGCTTGGCACTTGATGT |
| pEAK12R | GATGGAGGTGGACGTGTCAG |
| pDEST8F | TCTTCTACGGCAAGGTGCTG |
| pDEST8R | AAGCAAGTAAAACCTCTACA |

Underlined sequence = Kozak sequence
Bold = Start codon/Stop codon
Italic sequence = His tag

REFERENCES

Alarcon-Chaidez FJ et al., Parasite Immunol, 25: 69-77, 2003.
Alcami A, Nat Rev Immunol, 3: 36-50, 2003.
Aijamali MN et al., Insect Mol Biol, 12: 299-305, 2003.
Alouani S, Methods Mol Biol, 138: 135-141, 2000.
Anguita J et al., Immunity, 16: 849-859, 2002.
Baggiolini M et al., Annu Rev Immunol, 15: 675-705, 1997.
Baggiolini M, J Intern Med, 250: 91-104, 2001.
Beck CG et al., J Biol Chem, 276: 43270-43276, 2001.
Ben-Bassat A, Bioprocess Technol., 12:147-159, 1991
Brown A et al., J Pept Sci, 2:40-46, 1996.
Burns JM et al., J Biol Chem., 277:2785-2789, 2002.
Bursill CA et al., Circulation, 110: 2460-2466, 2004.
Chuang VT et al., Pharm Res., 19: 569-577, 2002.
Clackson et al., Nature, 352:624-628, 1991.
Cleland JL et al., Curr Opin Biotechnol, 12: 212-9, 2001.
Coleman R et al., Drug Discov Today, 6:1116-1126, 2001.
Dougherty DA, Curr Opin Chem Biol, 4: 645-52, 2000.
Fernandez EJ and Lolis E, Annu Rev Pharmacol Toxicol, 42:469-499, 2002.
Ferreira BR and Silva JS, Vet Immunol Immunopathol, 64: 279-293, 1998.
Gendel SM, Ann NY Acad SCI, 964: 87-98, 2002.
Gillespie RD et al., J Immunol, 166: 4319-4326, 2001.
Godessart N and Kunkel SL, Curr Opin Immunol, 13: 670-675, 2001.

Goding, Monoclonal Antibodies: Principles and Practice, Academic Press, (1986) pp. 59-103
Golebiowski A et al., Curr Opin Drug Discov Devel, 4: 428-34, 2001.
Graslund T et al., Protein Expr Purif., 9: 125-132, 1997.
Greenwald RB et al., Adv Drug Deliv Rev, 55: 217-250, 2003.
Gwakisa P et al., Vet Parasitol, 99:53-61, 2001.
Harris JM and Chess RB, Nat Rev Drug Discov, 2: 214-221, 2003.
Hill CA and Gutierrez JA, Med Vet Entomol, 17: 224-227, 2003.
Holt LJ et al., Trends Biotechnol, 21:484-490, 2003.
Hoogenboom and Winter, J. Mol. Biol., 227:381, 1991
Hruby VJ and Balse PM, Curr Med Chem, 7: 945-970, 2000.
Kipriyanov SM and Le Gall F, Mol Biotechnol, 26:39-60, 2004.
Kohler et al, Nature 256: 495, 1975
Jensen KK et al., J Virol, 77: 624-630, 2003.
Jones et al., Nature, 321:522-525, 1986
Li A, Drug Discov Today, 6: 357-366, 2001.
Lindow M et al., Trends Pharm Sci, 24: 126-130, 2003.
Loetscher P and Clark-Lewis I, J Leukoc Biol, 69: 881-884, 2001.
Luo B and Prestwich GD, Exp Opin Ther Patents, 11: 1395-1410, 2001.
Madden RD et al., Exp Appl Acarol, 32: 77-87, 2004.
Marshall SA et al., Drug Disc Today, 8: 212-221, 2003.
Marks et al., J. Mol. Biol., 222:581-597, 1991.
Mulenga A et al., Microbes Infect, 2: 1353-1361, 2000.
Murphy LR et al., Protein Eng, 13:149-152, 2000.
Murrell A et al., Mol Phylogenet Evol, 21: 244-258, 2001.
Nilsson J et al., Protein Expr Purif, 11: 1-16, 1997.
Pearson WR, Methods Mol Biol., 132:185-219, 2000.
Pillai O and Panchagnula R, Cur Opin Chem Biol, 5: 447-451, 2001.
Presta L, Curr Opin Struct Biol, 13: 519-525, 2003.
Pyo R et al., Am J Pathol, 164: 2289-2297, 2004.
Rapoport TA et al., Annu Rev Biochem., 65:271-303, 1996.
Rogov SI and Nekrasov AN, Protein Eng, 14: 459-463, 2001.
Scatchard G., Ann NY Acad. Sci. 51: 660-672, 1949
Schellekens H, Nat Rev Drug Disc, 1: 457-462, 2002.
Seet BT et al., Proc Natl Acad Sci USA, 98: 9008-9013, 2001.
Ullmann AJ et al., Exp Appl Acarol, 28: 107-126, 2002.
Vaitukaitis et al. J Clin Endocrinol Metab. 33, p. 988, 1971
Valenzuela JG, Am J Trop Med Hyg, 66: 223-224, 2002.
Vasserot AP et al., Drug Disc Today, 8: 118-126, 2003.
Van Valkenburgh HA and Kahn RA, Methods Enzymol., 344:186-193, 2002.
Villain M et al., Chem Biol, 8: 673-679, 2001.
Wang H et al., Exp Appl Acarol 1999, 23: 969-975, 1999.
Ward et al., Nature 341:544, 1989
Webb LM et al., FASEB J, 18: 571-573, 2004.

---

The invention claimed is:

1. An isolated polypeptide comprising:
   a) SEQ ID NO: 5;
   b) SEQ ID NO: 6;
   c) SEQ ID NO: 17;
   d) SEQ ID NO: 18; or
   e) a fusion protein comprising any one of a), b), c), or d) operably linked to a heterologous sequence selected from: an extracellular domain of a membrane-bound protein, an immunoglobulin constant region, a multimerization domain, a signal peptide, an export signal or a tag sequence.

2. The isolated polypeptide according to claim 1, wherein said polypeptide comprises SEQ ID NO: 5.

3. The isolated polypeptide according to claim 1, wherein said polypeptide comprises SEQ ID NO: 6.

4. The isolated polypeptide according to claim 1, wherein said polypeptide comprises SEQ ID NO: 17.

5. The isolated polypeptide according to claim 1, wherein said polypeptide comprises SEQ ID NO: 18.

6. The isolated polypeptide according to claim 1, wherein said polypeptide is a fusion protein comprising SEQ ID NO:5 operably linked to a heterologous sequence selected from: an extracellular domain of a membrane-bound protein, an immunoglobulin constant region, a multimerization domain, a signal peptide, an export signal or a tag sequence.

7. The isolated polypeptide according to claim 1, wherein said polypeptide is a fusion protein comprising SEQ ID NO:6 operably linked to a heterologous sequence selected from: an extracellular domain of a membrane-bound protein, an immunoglobulin constant region, a multimerization domain, a signal peptide, an export signal or a tag sequence.

8. The isolated polypeptide according to claim 1, wherein said polypeptide is a fusion protein comprising SEQ ID NO: 17 operably linked to a heterologous sequence selected from: an extracellular domain of a membrane-bound protein, an immunoglobulin constant region, a multimerization domain, a signal peptide, an export signal or a tag sequence.

9. The isolated polypeptide according to claim 1, wherein said polypeptide is a fusion protein comprising SEQ ID NO:18 operably linked to a heterologous sequence selected from: an extracellular domain of a membrane-bound protein, an immunoglobulin constant region, a multimerization domain, a signal peptide, an export signal or a tag sequence.

10. An isolated nucleic acid encoding a polypeptide according to claim 1.

11. The isolated nucleic acid according to claim 10, said nucleic acid encoding a polypeptide comprising SEQ ID NO: 5.

12. The isolated nucleic acid according to claim 10, said nucleic acid encoding a polypeptide comprising SEQ ID NO: 6.

13. The isolated nucleic acid according to claim 10, said nucleic acid encoding a polypeptide comprising SEQ ID NO: 17.

14. The isolated nucleic acid according to claim 10, said nucleic acid encoding a polypeptide comprising SEQ ID NO: 18.

15. The isolated nucleic acid according to claim 10, said nucleic acid encoding a fusion protein comprising SEQ ID NO:5 operably linked to a heterologous sequence selected from: an extracellular domain of a membrane-bound protein, an immunoglobulin constant region, a multimerization domain, a signal peptide, an export signal or a tag sequence.

16. The isolated nucleic acid according to claim 10, said nucleic acid encoding SEQ ID NO:6 operably linked to a heterologous sequence selected from: an extracellular domain of a membrane-bound protein, an immunoglobulin constant region, a multimerization domain, a signal peptide, an export signal or a tag sequence.

17. The isolated nucleic acid according to claim 10, said nucleic acid encoding a fusion protein comprising SEQ ID NO:17 operably linked to a heterologous sequence selected from: an extracellular domain of a membrane-bound protein, an immunoglobulin constant region, a multimerization domain, a signal peptide, an export signal or a tag sequence.

18. The isolated nucleic acid according to claim 10, said nucleic acid encoding a fusion protein comprising SEQ ID NO:18 operably linked to a heterologous sequence selected from: an extracellular domain of a membrane-bound protein, an immunoglobulin constant region, a multimerization domain, a signal peptide, an export signal or a tag sequence.

19. The isolated nucleic acid according to claim 10, wherein said nucleic acid molecule comprises SEQ ID NO: 3.

20. The isolated nucleic acid according to claim 10, wherein said nucleic acid molecule comprises SEQ ID NO: 4.

21. The isolated nucleic acid according to claim 10, wherein said nucleic acid molecule comprises SEQ ID NO: 15.

22. The isolated nucleic acid according to claim 10, wherein said nucleic acid molecule comprises SEQ ID NO: 16.

23. A cloning or expression vector comprising a nucleic acid according to claim 10.

24. An isolated host cell comprising a cloning or expression vector according to claim 23.

25. A method of preparing a polypeptide, comprising culturing a host cell according to claim 24 under conditions allowing or promoting expression of the polypeptide.

26. The method according to claim 25, further comprising purifying the protein.

27. The method according to claim 25, further comprising formulating the protein in a pharmaceutically acceptable excipient or diluent.

28. A method of inducing an immune response to a polypeptide according to claim 1 comprising administering a composition comprising a polypeptide according to claim 1 to an animal in an amount effective to induce an immune response to said polypeptide.

29. A method of reducing the chemotactic activity of MIP-1α or RANTES comprising contacting MIP-1α or RANTES with a composition comprising a pharmaceutically acceptable carrier or diluent and a polypeptide according to claim 1.

30. A pharmaceutical composition comprising a polypeptide of claim 1.

* * * * *

UNITED STATES PATENT AND TRADEMARK OFFICE
CERTIFICATE OF CORRECTION

PATENT NO. : 7,635,576 B2  Page 1 of 1
APPLICATION NO. : 11/722033
DATED : December 22, 2009
INVENTOR(S) : Amanda Proudfoot, Christine Power and Achim Frauenschuh It is certified that error appears in the above-identified patent and that said Letters Patent is hereby corrected as shown below:

Column 9,
Line 50, "This done then" should read --This clone then--.

Column 10,
Line 33, "non-ceavable" should read --non-cleavable--.

Column 13,
Line 27, "ChBP-598" should read --ChBP-59--.

Column 21,
Line 43, "llamas, to and alpacas" should read --llamas, and alpacas--.

Column 28,
Line 57, "volume of 101" should read --volume of 10 il--.

Column 38,
Line 43, "Aijamali" should read --Aljamali--.

Column 51,
Line 11, "encoding SEQ ID NO: 6" should read
--encoding a fusion protein comprising SEQ ID NO: 6--.

Signed and Sealed this

Twenty-second Day of June, 2010

David J. Kappos
*Director of the United States Patent and Trademark Office*

UNITED STATES PATENT AND TRADEMARK OFFICE
CERTIFICATE OF CORRECTION

PATENT NO. : 7,635,576 B2
APPLICATION NO. : 11/722033
DATED : December 22, 2009
INVENTOR(S) : Amanda Proudfoot, Christine Power and Achim Frauenschuh It is certified that error appears in the above-identified patent and that said Letters Patent is hereby corrected as shown below:

Column 28,
Line 57, "volume of 101" should read --volume of 10 µl--.

Signed and Sealed this

Tenth Day of August, 2010

David J. Kappos
*Director of the United States Patent and Trademark Office*